US009682235B1

(12) United States Patent
O'Mahony et al.

(10) Patent No.: US 9,682,235 B1
(45) Date of Patent: Jun. 20, 2017

(54) ELECTRICAL STIMULATION FOR PRESERVATION AND RESTORATION OF DIAPHRAGM FUNCTION

(71) Applicants: John O'Mahony, Maple Grove, MN (US); Patrick J. Wethington, Edina, MN (US)

(72) Inventors: John O'Mahony, Maple Grove, MN (US); Patrick J. Wethington, Edina, MN (US)

(73) Assignee: Stimdia Medical, Inc., Edina, MN (US)

( * ) Notice: Subject to any disclaimer, the term of this patent is extended or adjusted under 35 U.S.C. 154(b) by 0 days.

(21) Appl. No.: 15/378,460

(22) Filed: Dec. 14, 2016

Related U.S. Application Data

(60) Provisional application No. 62/267,095, filed on Dec. 14, 2015, provisional application No. 62/362,250, filed on Jul. 14, 2016, provisional application No. 62/359,972, filed on Jul. 8, 2016, provisional application No. 62/342,345, filed on May 27, 2016, provisional application No. 62/316,879, filed on Apr. 1, 2016, provisional application No. 62/304,509, filed on Mar. 7, 2016, provisional application No. 62/276,387, filed on Jan. 8, 2016, provisional application No. 62/387,262, filed on Dec. 23, 2015.

(51) Int. Cl.
*A61N 1/36* (2006.01)
*A61N 1/05* (2006.01)
*A61M 16/08* (2006.01)
*A61M 16/00* (2006.01)

(52) U.S. Cl.
CPC ....... *A61N 1/3601* (2013.01); *A61M 16/0833* (2014.02); *A61M 16/0875* (2013.01); *A61N 1/0502* (2013.01); *A61N 1/0551* (2013.01); *A61N 1/36017* (2013.01); *A61M 2016/0018* (2013.01); *A61M 2016/0027* (2013.01); *A61M 2016/0036* (2013.01); *A61M 2205/502* (2013.01)

(58) Field of Classification Search
None
See application file for complete search history.

(56) References Cited

U.S. PATENT DOCUMENTS

| 5,161,525 A | * | 11/1992 | Kimm | A61M 16/00 128/204.21 |
|---|---|---|---|---|
| 5,794,615 A | * | 8/1998 | Estes | A61M 16/00 128/204.23 |
| 6,015,388 A | * | 1/2000 | Sackner | A61B 5/08 600/529 |

(Continued)

FOREIGN PATENT DOCUMENTS

WO 2014207623 12/2014

OTHER PUBLICATIONS

Apr. 13, 2017 PCT Search Report (Serial No. PCT/US16/66542).

*Primary Examiner* — Brian T Gedeon
(74) *Attorney, Agent, or Firm* — Beck Tysver Evans, PLLC

(57) ABSTRACT

A system and method are presented that electrically stimulates the phrenic nerve whereby said stimulation results in muscle activation of the diaphragm as observed by a measurement of work or power of breathing associated with the inspiratory portion of a stimulated breath.

7 Claims, 23 Drawing Sheets

(56) References Cited

U.S. PATENT DOCUMENTS

| | | | | |
|---|---|---|---|---|
| 6,105,575 | A * | 8/2000 | Estes | A61M 16/00 128/204.21 |
| 6,360,740 | B1 * | 3/2002 | Ward | A61N 1/3601 128/200.24 |
| 7,283,874 | B2 * | 10/2007 | Penner | A61B 5/0031 607/33 |
| 7,792,585 | B1 | 9/2010 | Shelchuk | |
| 7,984,712 | B2 * | 7/2011 | Soliman | A61M 16/0051 128/202.22 |
| 8,406,885 | B2 | 3/2013 | Ignagni et al. | |
| 8,597,198 | B2 | 12/2013 | Sanborn et al. | |
| 8,881,725 | B2 * | 11/2014 | Sinderby | A61M 16/0051 128/204.18 |
| 9,027,552 | B2 * | 5/2015 | Angelico | A61M 16/0051 128/204.18 |
| 9,242,088 | B2 | 1/2016 | Thakkar et al. | |
| 9,308,337 | B2 * | 4/2016 | Heyer | A61M 16/0051 |
| 9,333,363 | B2 | 5/2016 | Hoffer et al. | |
| 2010/0071695 | A1 * | 3/2010 | Thiessen | A61M 16/0816 128/204.18 |
| 2012/0215278 | A1 * | 8/2012 | Penner | A61N 1/3601 607/42 |
| 2012/0290036 | A1 | 11/2012 | Karamanoglu et al. | |
| 2013/0030496 | A1 | 1/2013 | Karamanoglu et al. | |
| 2014/0123979 | A1 | 5/2014 | Doyle et al. | |
| 2015/0045810 | A1 | 2/2015 | Hoffer et al. | |
| 2015/0045848 | A1 | 2/2015 | Cho et al. | |
| 2015/0265833 | A1 | 9/2015 | Meyyappan et al. | |
| 2015/0283340 | A1 | 10/2015 | Zhang et al. | |
| 2015/0367127 | A1 | 12/2015 | Meyyappan et al. | |
| 2016/0220822 | A1 | 8/2016 | Hoffer et al. | |

* cited by examiner

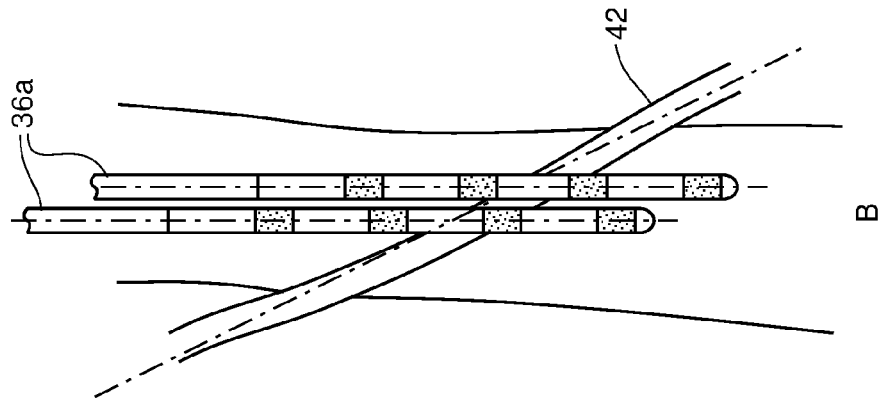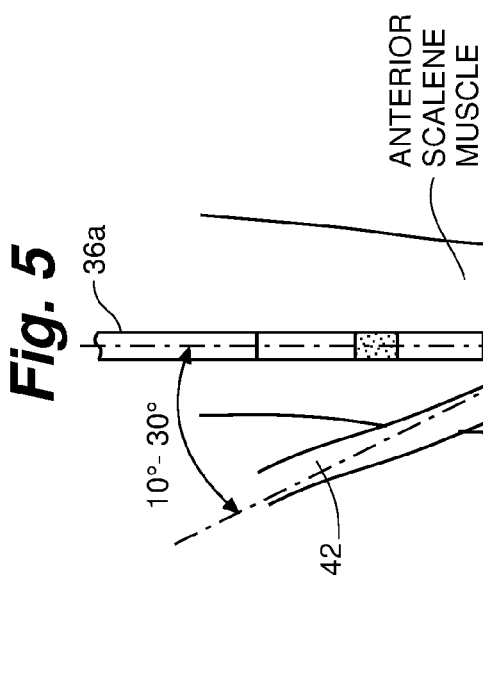

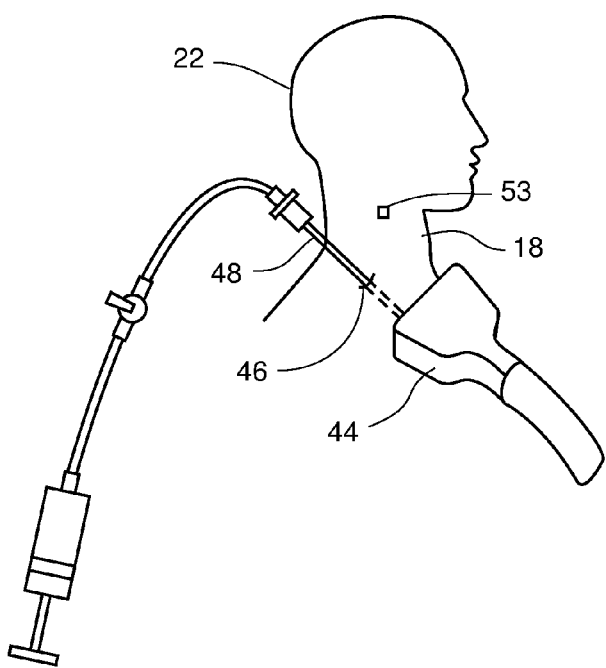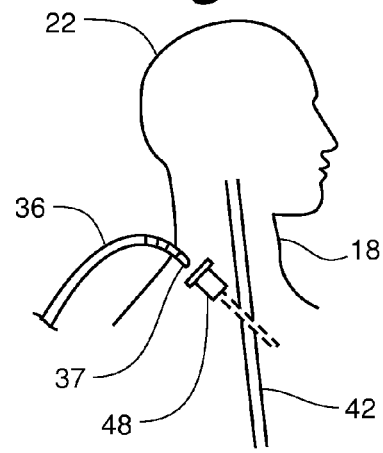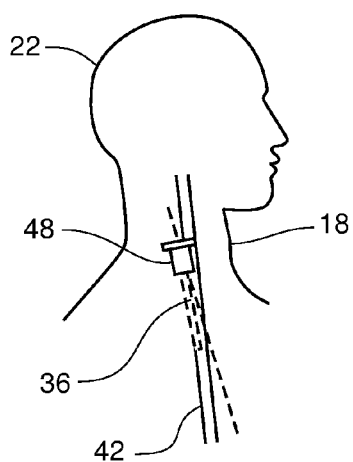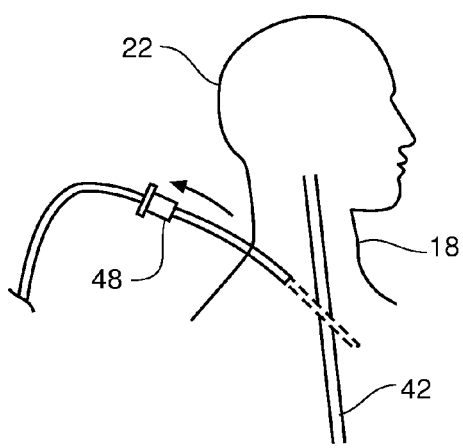

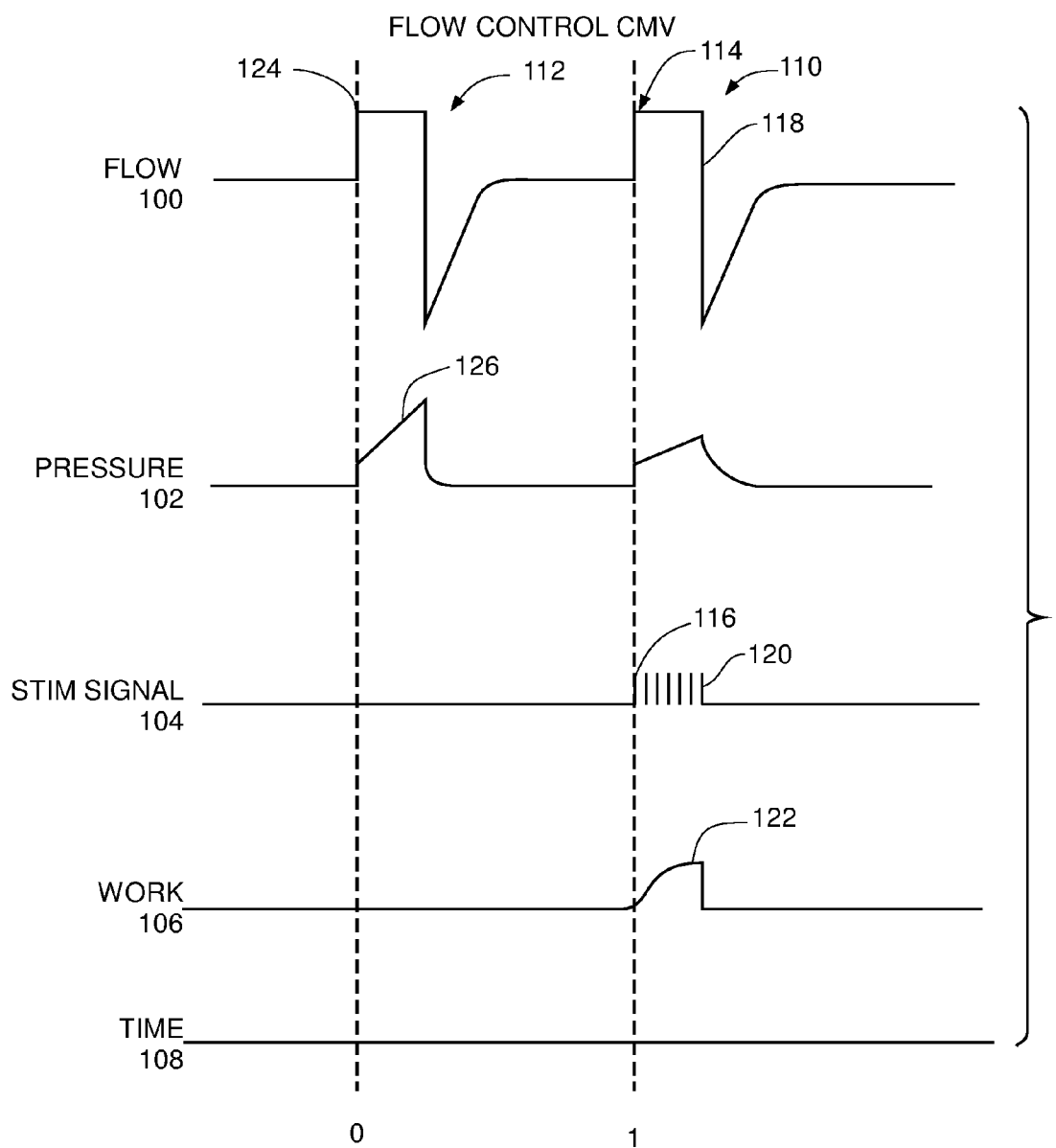

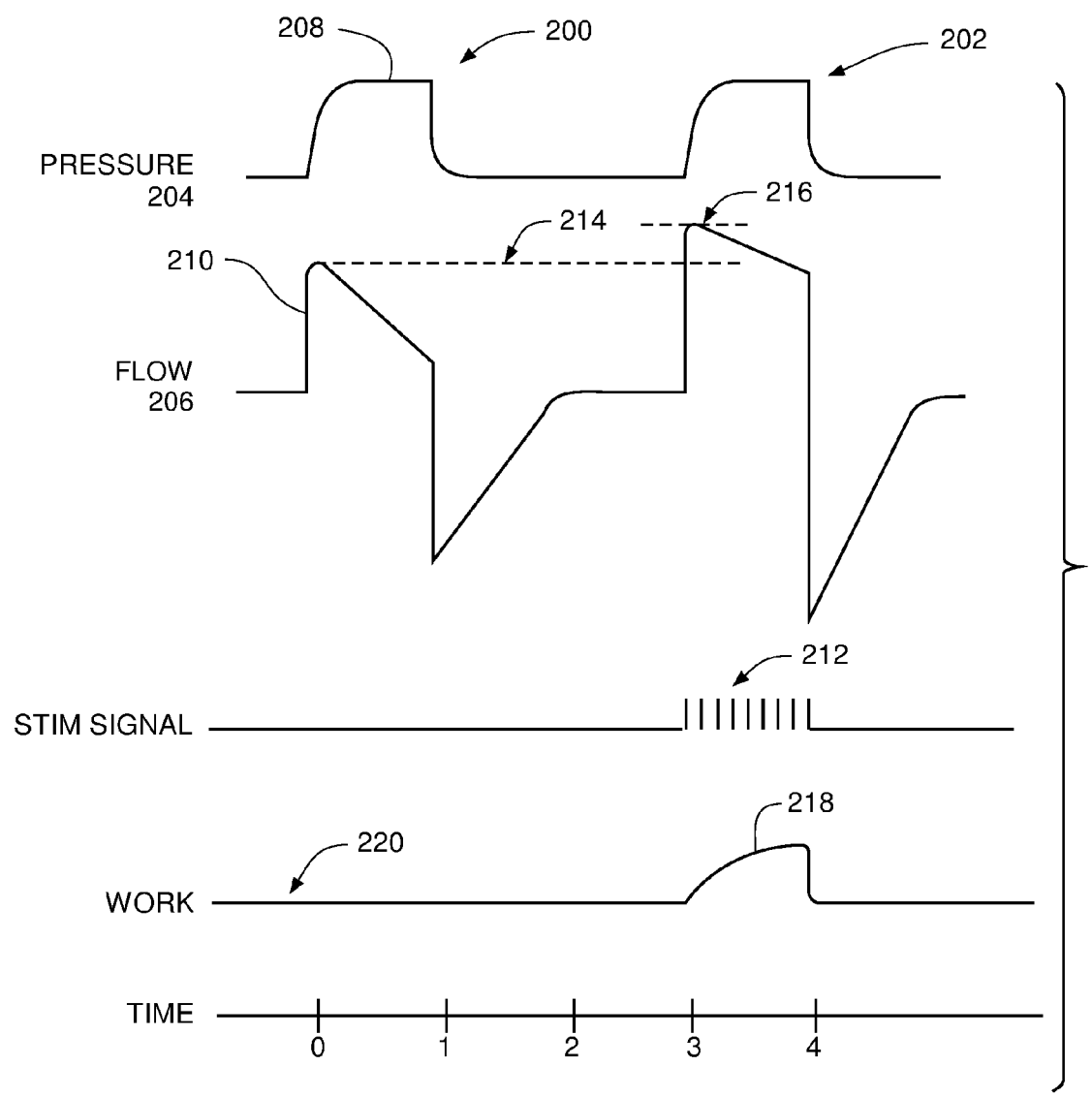

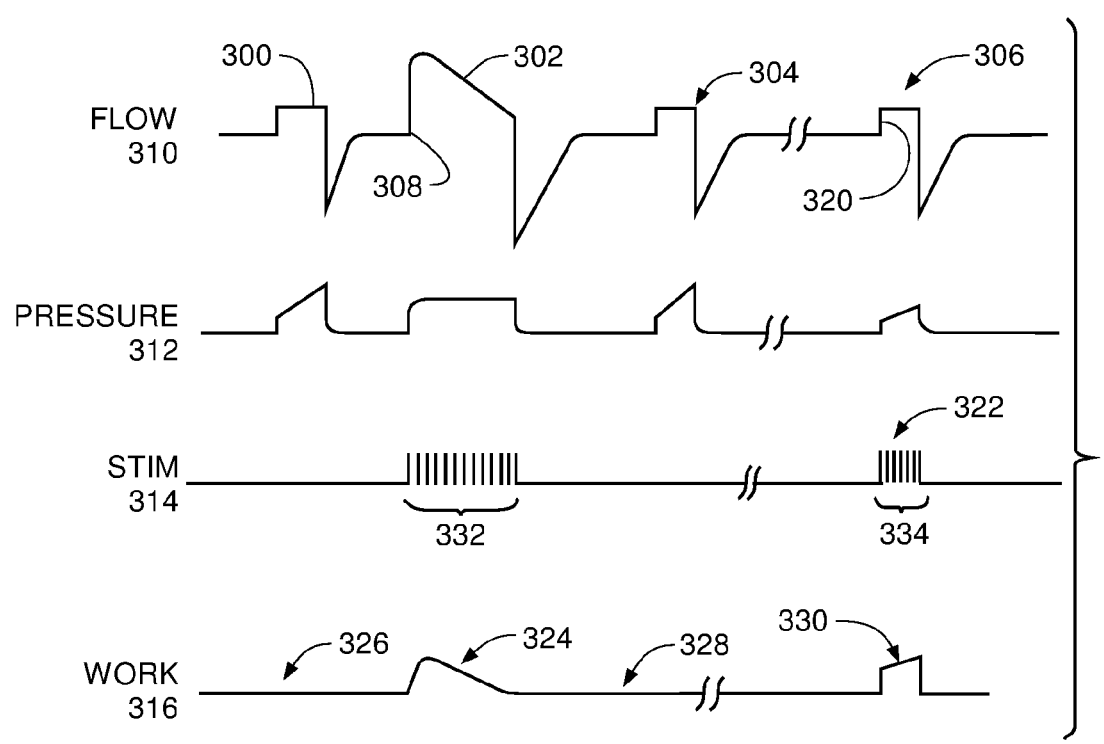

SIMV (PRESSURE CONTROL, PSV)

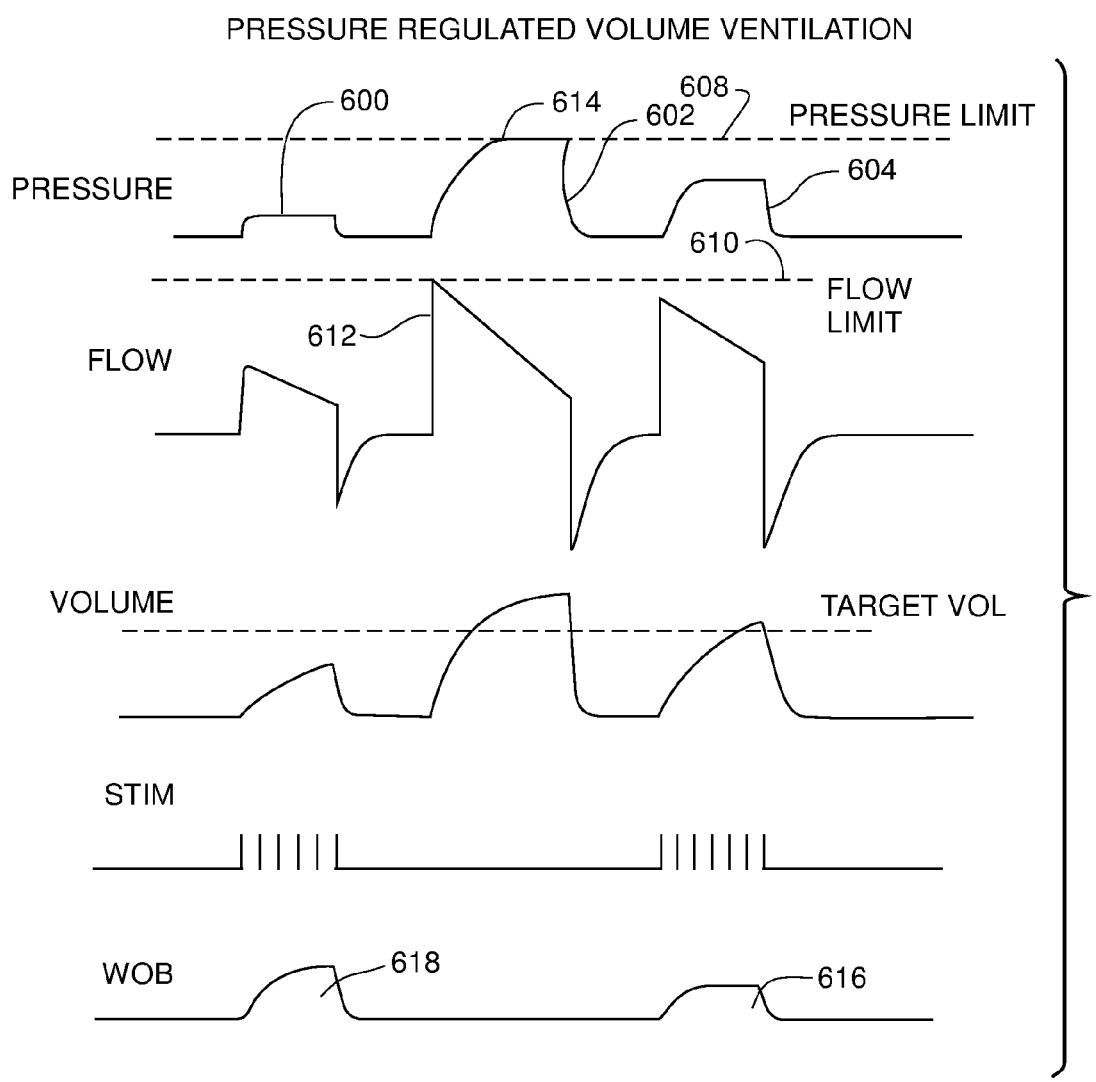

Fig. 17B

| BREATH | BREATH TYPE | STIMULATED YES/NO | PTP (cmH2O SEC.) | PTP DIFFERENCE (cmH2O SEC.) | WOB (JOULES/L) |
|---|---|---|---|---|---|
| 700 | VCV 60 Lpm | YES | 9.0 | NO PREVIOUS DATA | 0.36 |
| 702 | VCV 60 Lpm | NO | 13.6 | | |
| 704 | VCV 60 Lpm | YES | 9.0 | 4.6 | 0.36 |
| 706 | VCV 120 Lpm | NO | 13.6 | | |
| 708 | VCV 60 Lpm | YES | 10.5 | 3.1 | 0.37 |
| 710 | VCV 60 Lpm | NO | 13.6 | | |
| 712 | VCV 60 Lpm | YES | 10.5 | 3.1 | 0.37 |
| 714 | PCV 20 cmH2O | NO | 17.0 | | |
| 716 | PCV 20 cmH2O | YES | 18.5 | -1.5 | 0.41 |
| 718 | PCV 20 cmH2O | NO | 17.0 | | |
| 720 | PCV 20 cmH2O | YES | 18.5 | -1.5 | 0.41 |
| 722 | PCV 20 cmH2O | NO | 17.0 | | |
| 724 | PCV 20 cmH2O | YES | 18.5 | -15 | 0.41 |
| 726 | PCV 20 cmH2O | NO | 17.0 | | |
| 728 | PCV 20 cmH2O | YES | 19.0 | -2.0 | 0.41 |
| 730 | PCV 20 cmH2O | NO | 18.0 | | |
| 732 | PCV 10 cmH2O | YES | 5.5 | 12.5 | 0.39 |
| 734 | PCV 10 cmH2O | NO | 4.5 | | |
| 736 | PCV 10 cmH2O | YES | 5.5 | -1.0 | 0.41 |
| 738 | PCV 10 cmH2O | NO | 4.5 | | |
| 740 | PCV 10 cmH2O | YES | 5.5 | -1.0 | 0.41 |

Fig. 19A

| SETTINGS PARAMETER | DESCRIPTION | RANGE |
|---|---|---|
| STIMULATION WAVEFORM | | |
| SETUP OF STIMULATION ELECTRODES | | |
| SWITCH POLARITY | INVERT POLARITY OF ELECTRODES. | POSITIVE AND NEGATIVE |
| SWITCH ELECTRODE PAIR | SWITCH TO NEXT COMBINATION OF ELECTRODE PAIRS. WITH 4 ELECTRODES, THERE ARE 2↑4 = 16 COMBINATION WHICH COULD BE STIMULATED. GIVEN THAT CHANGES IN ELECTRODE POLARITY PAIRS ARE ALREADY COVERED THIS NUMBER OF COMBINATIONS IS REDUCED TO 2↑3 = 8 PAIRED COMBINATIONS. | |
| FLOW TRIGGERING | | |
| INSPIRED FLOW TRIGGER SENSITIVITY | THIS IS THE INSPIRATORY FLOW ABOVE WHICH INSPIRATION IS DETECTED. | 3 TO 30 Lpm |
| EXPIRED FLOW TRIGGER SENSITIVITY | THIS IS THE INSPIRATORY FLOW OR EXPIRATORY FLOW BELOW WHICH EXPIRATION IS DETECTED. IN THE CASE OF A PLATEAU IT MAY BE NECESSARY TO SET THE EXPIRED TRIGGER FLOW NEGATIVE DURING PLATEAU THE INSPIRED FLOW CEASES AND IS 0 Lpm. EXHALATION BEGINS WHEN THE EXHALATION VALVE OF THE VENTILATOR OPENS AND FLOW IS CONVENTIONALLY SEEN AS NEGATIVE EXITING THE PATIENT | -30 TO 30 Lpm |
| PULSE STIMULATION SETTINGS | | |
| PULSE SHAPE | THE CURRENT PULSE SHAPE CAN BE SET TO BALANCED SYMMETRICAL BIPHASIC OR BALANCED ASYMMETRICAL BIPHASIC. THE AREA UNDER EACH THE NEGATIVE AND POSITIVE PULSE ARE ALWAYS EQUAL WITH BALANCED BIPHASIC. | SQUARE OR RAMPED |
| PULSE RATE | THIS IS THE FREQUENCY AT WHICH CURRENT PULSE OCCUR WITHIN A BREATH. | 5 TO 50 Hz |
| PULSE WIDTH POSITIVE | WIDTH OF THE POSITIVE CURRENT PULSE. | 50 TO 200 uS |
| PULSE WIDTH NEGATIVE | WIDTH OF THE POSITIVE CURRENT PULSE. | 50 TO 200 uS |

Fig. 19B

| STIMULATION FREQUENCY AND WAVEFORM TYPE | | |
|---|---|---|
| STIMULATION WAVEFORM | ENABLES THE USER TO SET A SQUARE WAVE (CONSTANT) OR RAMPED WAVEFORM IN TERMS OF SUCCEEDING CURRENT PULSES. | SQUARE OR RAMPED |
| BREATH STIM RATE | FREQUENCY AT WHICH BREATHS ARE STIMULATED | 1:1 TO 1:20 |
| CURRENT SETTINGS | | |
| STIMULATION CURRENT LEFT - SQUARE | LEFT LEAD: STIMULATION CURRENT FOR A SQUARE WAVE OF CURRENT. CURRENT IS CONSTANT | 0.5 TO 25 mA |
| STIMULATION CURRENT RIGHT - SQUARE | RIGHT LEAD: STIMULATION CURRENT FOR A SQUARE WAVE OF CURRENT. CURRENT IS CONSTANT | 0.5 TO 25 mA |
| STIMULATION CURRENT LEFT START - RAMPED | LEFT LEAD: INITIAL STIMULATION CURRENT. CURRENT IS RAMPED DURING BREATH AT THE SLOPE DEFINED. | 0.5 TO 25 mA |
| STIMULATION CURRENT LEFT END - RAMPED | LEFT LEAD: MAXIMUM STIMULATION CURRENT. CURRENT IS RAMPED DURING BREATH BUT WILL NOT BE ALLOWED TO EXCEED THIS MAXIMUM LEVEL. | STIMULATION CURRENT LEFT START TO 25 mA |
| STIMULATION CURRENT LEFT SLOPE - RAMPED | LEFT LEAD: SLOPE AT WHICH CURRENT IS RAMPED. | 0.5 TO 100 mA/s |
| STIMULATION CURRENT RIGHT START - RAMPED | RIGHT LEAD: INITIAL STIMULATION CURRENT. CURRENT IS RAMPED DURING BREATH AT THE SLOPE DEFINED. | 0.5 TO 25 mA |
| STIMULATION CURRENT RIGHT END - RAMPED | RIGHT LEAD: MAXIMUM STIMULATION CURRENT. CURRENT IS RAMPED DURING BREATH BUT WILL NOT BE ALLOWED TO EXCEED THIS MAXIMUM LEVEL | STIMULATION CURRENT LEFT START TO 25 mA |
| STIMULATION CURRENT RIGHT SLOPE - RAMPED | RIGHT LEAD: SLOPE AT WHICH CURRENT IS RAMPED | 0.5 TO 100 mA/s |

Fig. 19C

| | | |
|---|---|---|
| WORK OF BREATHING (WOB) | | |
| | LUNG COMPLIANCE | 0.1 TO 500 ml/cmH2O |
| | LUNG RESISTANCE | 0.1 TO 500 cmH2O/L/s |
| GENERAL SYSTEM FUNCTIONS | | |
| | SET DATE AND TIME | US FORMAT |
| | AUDIO VOLUME | UNITLESS NUMBER 1 TO 10 |
| | LCD LED BRIGHTNESS | UNITLESS NUMBER 1 TO 10 |
| | TURN ON/OFF STIMULATION | ON/OFF |

(904)

| DISPLAYED PARAMETER | DESCRIPTION | RANGE |
|---|---|---|
| WOB (JOULES/L) | MEASUREMENT OF WOB FOR A BREATH. | 0 TO 3 JOULES/L |
| PWYE: WYE PRESSURE (cmH2O) | MEASUREMENT OF WYE PRESSURE | -100 TO 100 cmH2O |
| QWYE: WYE FLOW (Lpm) | MEASUREMENT OF WYE FLOW IN AND OUT OF PATIENT | -300 TO 300 Lpm |
| PMUS: DIAPHRAGM MUSCLE (cmH2O) | MEASUREMENT OF THE DIAPHRAGM MUSCLE EFFORT IN cmH2O | -100 TO 100 cmH2O |

| ALARM NAME | DETECTION CRITERIA | DESCRIPTION | ALARM REACTION | ENABLE DISABLE | NAME/ UNITS | RANGE |
|---|---|---|---|---|---|---|
| RIGHT LEAD IMPEDANCE TOO HIGH | THE MEASURED LEAD IMPEDANCE IS GREATER THAN THE MAXIMUM LEAD IMPEDANCE ALLOWED FOR THE RIGHT LEAD FOR 2 BREATHS. | • CHECK THAT THE LEAD IS CONNECTED.<br>• CHECK THAT THE LEAD IS NOT FRACTURED<br>• DISCONNECT AND RECONNECT THE LEAD CONNECTIONS BETWEEN LEAD AND EXTENSION CABLE AND CONSOLE. | SAFE STATE | NO | IMPEDANCE Ω | 500 TO 5000 OHMS |
| RIGHT LEAD IMPEDANCE TOO LOW | THE MEASURED LEAD IMPEDANCE IS LESS THAN THE MINIMUM LEAD IMPEDANCE ALLOWED FOR FOR THE RIGHT LEAD FOR 2 BREATHS. | • DISCONNECT AND RECONNECT LEAD CONNECTIONS BETWEEN EXTENSION CABLE AND CONSOLE ENSURING THEY ARE DRY.<br>• DISCONNECT THE LEAD CONNECTIONS BETWEEN EXTENSIONS CABLE AND MULTIPOLE LEAD ENSURING THEY ARE DRY.<br>• CHECK FOR A SHORT IN THE LEAD.<br>• REPLACE LEAD IF NECESSARY | SAFE STATE | NO | IMPEDANCE Ω | 50 TO 1000 OHMS |
| LEFT LEAD IMPEDANCE TO HIGH | THE MEASURED LEAD IMPEDANCE IS GREATER THAN THE MAXIMUM LEAD IMPEDANCE ALLOWED FOR THE LEFT LEAD FOR 2 BREATHS. | • CHECK THAT THE LEAD IS CONNECTED.<br>• CHECK THAT THE LEAD IS NOT DAMAGED OR FRACTURED.<br>• DISCONNECT AND RECONNECT THE LEAD CONNECTIONS BETWEEN LEAD AND EXTENSION CABLE AND THE CONSOLE AND EXTENSION CABLE. | SAFE STATE | NO | IMPEDANCE Ω | 500 TO 5000 OHMS |

Fig. 20A-1

| | | | | |
|---|---|---|---|---|
| LEFT LEAD IMPEDANCE TOO LOW | THE MEASURED IMPEDANCE IS LESS THAN THE MINIMUM LEAD IMPEDANCE ALLOWED FOR THE RIGHT LEAD FOR 2 BREATHS. | • DISCONNECTED AND RECONNECT LEAD CONNECTIONS BETWEEN EXTENSION CABLE AND CONSOLE ENSURING THEY ARE DRY.<br>• DISCONNECT THE LEAD CONNECTIONS BETWEEN EXTENSION CABLE AND MULTIPOLE LEAD ENSURING THEY ARE DRY.<br>• CHECK FOR A SHORT IN THE LEAD.<br>• REPLACE LEAD IF NECESSARY. | SAFE STATE | NO | IMPEDANCE $\Omega$ | 500 TO 5000 OHMS |
| INSPIRATORY PERIOD TOO LONG | THE MEASURED INSPIRATORY PERIOD IS LONGER THAN THE ALLOWED MAXIMUM INSPIRATORY PERIOD. | THE INSPIRATION PERIOD IS GREATER THAN X SECONDS. ADJUST THE INSPIRATORY AND EXPIRATORY FLOW TRIGGERING AS NECESSARY. | SAFE STATE | NO | SECONDS | USER SETTABLE 0.5 TO 6 SECONDS<br><br>DEFAULT 3 SECONDS |
| BREATH RATE TOO HIGH | THE MEASURED BREATH RATE IS HIGHER THAN THE ALLOWED $f_{TOT}$ | THE RESPIRATORY RATE IS AFTER CHANGING SIGNIFICANT OR IS TOO HIGH. | SAFE STATE | YES | $f_{TOT}=$ BREATHS PER MINUTE (BPM)<br><br>(FREQ. TOTAL) | USER SETTABLE 10 TO 50 BPM<br><br>DEFAULT 15 |

*Fig. 20A-2*

| | | | | | |
|---|---|---|---|---|---|
| INCREASED WORK | THE MEASURED WORK EXERTED BY THE PATIENT IS GREATER THAN THE MAXIMUM ALLOWABLE LEVEL FOR 10 BREATHS. | THE WORK IS TOO HIGH.<br>• REDUCE THE PULSE RATE, STIMULATION CURRENT. CONSIDER MOVING TO A RAMPED WAVEFORM IS NOT ALREADY SELECTED.<br>• CHECK THE CORRECT PATIENT COMPLIANCE AND RESISTANCE WERE ENTERED. | SAFE STATE | NO | J OR J/L<br>(JOULES/LITER) | USER SETTABLE 0.01 TO 2.00 J/L |
| DECREASED WORK | THE MEASURED WORK EXERTED BY THE PATIENT IS LESS THAN THE MINIMUM ALLOWABLE LEVEL FOR 10 BREATHS. | THE WORK IS TOO LOW.<br>• CONSIDER SWITCHING STIMULATION ELECTRODES<br>• INCREASE STIMULATION LEVEL BY ADJUSTING CURRENT AMPLITUDE OR FREQUENCY OF STIMULATION.<br>• CHECK THE CORRECT PATIENT COMPLIANCE AND RESISTANCE WERE ENTERED. | SAFE STATE | NO | J OR J/L | USER SETTABLE 0.01 TO 2.00 J/L |

Fig. 20B

| ALARM NAME | DETECTION CRITERIA | DESCRIPTION | ALARM REACTION | ENABLE DISABLE | NAME/ UNITS | RANGE |
|---|---|---|---|---|---|---|
| APNEA/ ELECTRICAL STIMULATION IS NOT OCCURRING | THE PEPNS SYSTEM HAS NOT DETECTED ANY BREATHS FOR SET APNEA PERIOD | THE SYSTEM HAS NOT DETECTED ANY BREATHS IN 20 SECONDS: CHECK: • THE WYE FLOW SENSOR IS CONNECTED TO THE PATIENT • THE DIFFERENTIAL PRESSURE TUBING IS CONNECTED TO THE FLOW SENSOR AND CONSOLE. ADJUST THE INSPIRATORY AND EXPIRATORY FLOW TRIGGERING AS NECESSARY. | CONTINUE OPERATION | YES | SECONDS | USER SETTABLE 10 TO 60 SECONDS. DEFAULT: 15 SECONDS |
| NO FLOW CHANGES DETECTED | THE WYE FLOW SENSOR HAS NOT MEASURED ANY CHANGES IN FLOW (QWYE VARIANCE < 5 Lpm AND QWYE > -5 Lpm FOR 20 SECONDS | NO WYE FLOW CHANGES MEASURED. CHECK: • THE WYE FLOW SENSOR IS CONNECTED TO THE PATIENT WYE. • THE DIFFERENTIAL PRESSURE TUBING IS CONNECTED TO THE FLOW SENSOR AND CONSOLE. | CONTINUE OPERATION | NO | NA | NA |
| NO PRESSURE CHANGES DETECTED | THE WYE PRESSURE SENSOR HAS NOT MEASURED ANY CHANGES IN FLOW (PWYE VARIANCE < 2 cmH2O AND QWYE > -2 cmH2O FOR 20 SECONDS | NO PRESSURE CHANGES OR PEEP DETECTED. • THE PRESSURE SENSOR IS CONNECTED TO THE PATIENT TUBING CIRCUIT. • THE PRESSURE SENSOR TUBING IS CONNECTED TO THE PATIENT TUBING CIRCUIT AND CONSOLE. | CONTINUE OPERATION | NO | NA | NA |

ELECTRICAL STIMULATION FOR PRESERVATION AND RESTORATION OF DIAPHRAGM FUNCTION

CROSS REFERENCE TO RELATED CASES

The present application claims priority to the following provisional applications: U.S. 62/267,095, entitled: Magnetic Stimulation for Control of the Lung Diaphragm, filed on Dec. 14, 2015; U.S. 62/362,250, entitled: Multiple Electrode Lead System, filed on Jul. 14, 2016; U.S. 62/359,972, entitled: Device and Method for Treatment of Ventilator Induced Diaphragm Atrophy, filed on Jul. 8, 2016; U.S. 62/342,345, entitled: Phrenic Nerve Stimulation and Diaphragmatic Pacing System and Method, filed on May 27, 2016; U.S. 62/316,879, entitled: Peripheral Nerve Stimulator and Method, filed Apr. 1, 2016; U.S. 62/304,509, entitled: Method and Apparatus for Stimulating Peripheral Nerves, filed on Mar. 7, 2016; U.S. 62/276,387, entitled: Subcutaneous Electrical Stimulation for Control of the Lung Diaphragm, filed on Jan. 8, 2016; and U.S. 62/387,262, entitled: Temporary Electrical Stimulation for Control of the Lung Diaphragm, filed on Dec. 23, 2015. The entire contents of each of the above referenced provisional applications being incorporated herein by reference.

FIELD OF THE INVENTION

Embodiments of the present disclosure are directed to medical devices, systems and their methods of use for providing noninvasive percutaneous and subcutaneous electrical stimulation to a patient subjected to mechanical ventilation, in order to mitigate the effects of ventilator-induced diaphragmatic dysfunction. Embodiments include devices for controlling, activating, and otherwise interacting with the phrenic nerve, and thereby the diaphragm, of a patient while the patient is undergoing mechanical ventilation.

BACKGROUND

Mechanical ventilation (MV) is used clinically to maintain gas exchange in patients that require assistance in maintaining adequate alveolar ventilation. Common indications for MV include respiratory failure, heart failure, surgery, etc. Although MV can be a life-saving intervention for patients suffering from respiratory failure, prolonged MV can promote diaphragmatic atrophy and contractile dysfunction, which is referred to as ventilator-induced diaphragm dysfunction (VIDD). Extended time on the ventilator may result in VIDD and thereby increase health care costs and greatly increase patient morbidity and mortality. Research reveals that 18-24 h on MV is sufficient to develop VIDD in both laboratory animals and humans.

2.1 million patients are ventilated in United States each year representing 36% of the ICU population. The estimated annual cost to manage ventilated patients in the US each year is 27 billion representing 12% of all hospital costs. It has been found that approximately 60% of the ICU patient population intubated are scheduled for extubation and weaning. Unfortunately, nearly 45% of patients receiving invasive ventilation therapy in the ICU have difficulty weaning and develop some form of dependency on the ventilator. This often leads to the need to extend the patients ICU/CCU stay beyond what is typically required for the original medical condition since many encounter prolonged weaning periods. The projected number of patients requiring prolonged acute mechanical ventilation on an annual basis in the US is expected to grow to be greater than 600,000 patients by the year 2020 with the overall cost of managing these patients exceeding $64 billion.

Animal models have shown that maintaining some level of stimulation to keep the diaphragm working when on a ventilator is enough to prevent or reduce atrophy. Unfortunately having a patient breath spontaneously or in assist mode from the initiation of ventilation is not always possible due to the level of sedation and/or disease state.

In these cases, phrenic nerve pacing is a viable alternative to control the level of effort exerted by the patient and also in cases where the patient has become ventilator dependent and requires a training regime of pacing to strengthen their muscles. Phrenic nerve pacing in animals has also been shown to prevent diaphragm atrophy. Pacing the phrenic nerve in patients who suffer from spine injury who have lost the ability to breath, has be shown to reverse the effect of atrophy over a 6 months training period where the diaphragm has not been used in years. It is generally better to prevent a disease condition rather than remediate it. Initiating stimulation early in the regime of ventilation will most likely have the most profound effect on reducing time to extubation.

Methods currently exist to electrically stimulate the phrenic nerve in chronically ventilated patients as an alternative to mechanical positive pressure ventilation, to avoid some of the potential side effects of long term ventilation already mentioned. More recently central sleep apnea events have been reduced with the use of implanted phrenic nerve pacing at the onset of apnea. Phrenic nerve pacing has also been achieved with the use of trans venous electrical stimulation. Patients who have permanent respiratory insufficiency due to absence or reduction in a central respiratory drive descending from the brain stem (C3, C4 and C5) are now using commercially available pacing products to pace the diaphragm muscle by electrically stimulating the phrenic nerves using implanted electrodes. These implanted stimulation devices use some form of phrenic nerve cuffs, or diaphragm electrodes all of which require invasive surgeries. The feasibility of such techniques to prevent diaphragm atrophy or wean patients from a ventilator are limited by the cost and risks associated with permanently implanted phrenic nerve pacing electrodes and are not a viable alternative for VIDD patients.

Diaphragm muscle pacing, phrenic nerve pacing, and combined intercostal and unilateral diaphragm pacing techniques are currently being used to wean patients without respiratory drive from ventilators in the chronic setting of ventilation and reduce the incidence of infection, atelectasis, and respiratory failure. There exists the need for a short term pacing alternative which can be easily connected to a patient in the ICU or post-surgery or similar setting to wean or prevent VIDD from occurring.

Embodiments described herein seek to meet this need by providing a diaphragmatic stimulation system which includes an electrical lead(s) component that is readily employed without the need of a permanent or surgical implantation. The system measures the level of effort in the patient's breathing. The level of stimulation is titrated with that level of effort measurement. Taken together these embodiments provide a less invasive system that can accommodate modest patient motion and function well within the context of a surgical or ICU recovery setting.

Embodiments of the present disclosure provide a system and methods of its use which when properly utilized, reduce the occurrence of VIDD by providing stimulation to the diaphragm of a patient undergoing MV and thereby provide improved patient outcomes if/when transitioning from MV and provide reduced healthcare costs.

SUMMARY

Embodiments of the system disclosed herein may be collectively referred to as a Percutaneous Electrical Phrenic Nerve Stimulation (PEPNS) system. Embodiments of the PEPNS system include both medical devices as well as methods of using those devices to provide stimulation and/or pacing to the diaphragm of a patient via electrical stimulation of the phrenic nerve so as to aid in preventing the occurrence of VIDD and to wean a patient from a mechanical ventilator. The PEPNS system includes a pulse generator console (or stimulator), called the Stimulator/Controller (S/C) throughout the disclosure, lead electrodes connected to the console for stimulating the phrenic nerve, as a well as a wye flow and pressure sensor that is used for detecting the inspiration and exhalation from the patient and measuring pressure at the ventilator pneumatic circuit wye.

In use, the wye flow and pressure sensor are supplied and inserted between a mechanical ventilator and the patient. The wye provides flow and pressure information to the console. A graphical user interface (GUI) on or adjacent to the console is used to permit physician or technician interaction with the stimulator. In general, the physician will set electrical pulse parameters and observe measurements on the GUI.

The leads of the system include two sets of multiple stimulation electrodes connected to the stimulator console by cables. The leads are inserted subcutaneously into the patient's neck and positioned adjacent to the phrenic nerve. The stimulator is then activated by the operating physician or technician to provide electrical pulse(s) to the phrenic nerve, and thus stimulate the diaphragm. Electrical pulses are delivered to the phrenic nerve by those electrodes along the leads that are in an optimized position adjacent to the nerve.

As the patient is transitioned from a fully ventilator dependent state the present system will shorten the weaning period and provide patient specific information to the physician to allow a rapid and accurate assessment of the patient's readiness to come off the mechanical ventilator.

BRIEF DESCRIPTION OF THE DRAWINGS

Throughout the several views of the drawing identified below reference numerals indicate identical structures.

FIG. 2a is a schematic view of one embodiment of the four electrode (pole) lead of the lead system component of the PEPNS system shown in FIG. 1a.

FIG. 2b is a schematic and block diagram view showing the electrical relationship between an embodiment of the lead system and the C/S as seen in FIGS. 1a and 2a.

FIG. 5 is a detailed view of the image shown in FIGS. 3-4 with more complete anatomical detail of the relative position of the first lead to the phrenic nerve illustrated.

FIG. 6 is the same view of the patient anatomy shown in FIG. 5 but with the potential for repositioning the lead being depicted.

FIGS. 7-10 depict a method of inserting a lead into the neck of the patient shown in FIG. 1a.

FIG. 11 is a sequence of graphical panels depicting waveforms associated with a flow control regimen of the mechanical ventilator and the PEPNS system shown in FIG. 1a.

FIG. 12 is a series of graphical panels depicting waveforms associated with a pressure control regimen of a mechanical ventilator and the PEPNS system shown in FIG. 1a.

FIG. 13 is a series of graphical panels depicting waveforms associated with a Synchronized Intermittent Mandatory Ventilation (SIMV) mode in a flow control regimen with pressure support ventilation in use with the PEPNS system shown in FIG. 1a.

FIG. 14 is a series of graphical panels depicting waveforms associated with a (SIMV) mode in a pressure control regimen with pressure support ventilation as may be used with the PEPNS system shown in FIG. 1a.

FIG. 15 is a series of graphical panels depicting waveforms associated with a bi-level ventilator modality with pressure support ventilation as may be used with the PEPNS system shown in FIG. 1a.

FIG. 16 is a series of graphical panels depicting waveforms associated with a pressure regulated volume ventilation setting of the mechanical ventilator in use with the PEPNS system shown in FIG. 1a.

FIG. 17 B is a table that shows calculated differences between the two different techniques set forth in FIG. 17A.

FIGS. 19A-19C are tables that reflects the input parameters to the graphic user interface of the stimulator/controller.

FIG. 20A, FIG. 20A-1, and FIG. 20A-2 is a table of alarm conditions.

FIG. 20B is a table of alarm conditions.

DETAILED DESCRIPTION OF THE DRAWINGS

Figure 1A:
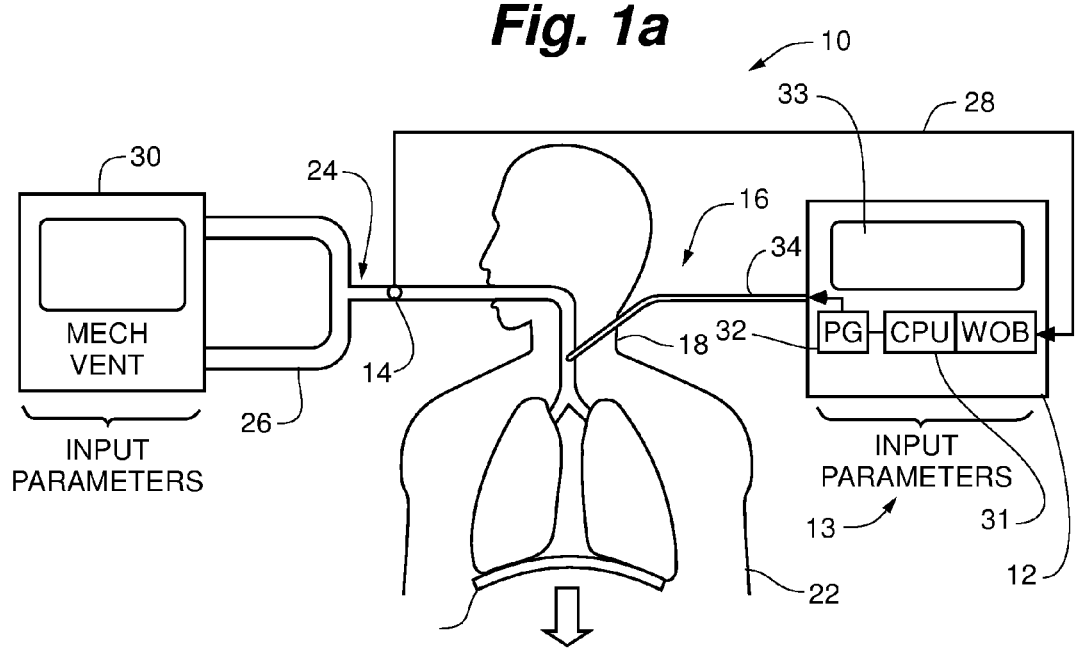
FIG. 1a is a schematic view of an embodiment of the PEPNS system shown in use with a patient and ventilator.

In FIG. 1a an embodiment of the PEPNS system 10 is shown in a typical environment of use. As is shown the PEPNS system 10 includes an operating console or stimulator/controller 12 which is in communication with an instrumented wye sensor 14 and an electrical stimulation lead assembly 16.

In order to stimulate the diaphragm 20 of a patient 22 the lead system 16 must be properly positioned percutaneously in the neck 18 of a patient 22. Current from the lead system electrically stimulates the phrenic nerve. To monitor the patient and determine that the level of stimulation is in fact sufficient to move the patients diaphragm 20 in the manner desired, the instrumented wye sensor 14 is placed in the breathing circuit tubing 26 of the mechanical ventilator 30 (MV) and measurements carried out by the S/C 12.

The instrumented wye sensor is pneumatically connected to the MV tube circuit 26 to measure both flow and pressure in the wye 24. There are a number of alternative methods for positioning sensors for measuring wye flow and pressure. The wye sensor 14 is electrically coupled to the stimulator/controller 12. The stimulator/controller 12 has processor or CPU 31 and an integrated pulse generator 32 to supply an electrical output delivered to the lead system 16 via a lead cable 34.

Data received from the wye sensor 14 and lead system 16, as well as the output parameters of the pulse generator 32 are displayed on a display or graphical user interface (GUI) 33 of the stimulator/controller 12. The GUI 33 may be a separate unit or device, such as a monitor, or maybe a dedicated component of the stimulator/controller 12. It will likely have both a touch screen for entering information and a high resolution display for displaying various information to the user.

Turning now to the lead system 16, as mentioned above the lead system 16 comprises a unitary lead body having a distal end with at least four electrodes and a proximal end having a set of terminals for connection to the S/C. In the embodiment shown in FIG. 2*a*, the lead 36 is a multipolar lead having at least four electrodes 38 (*a-d*) contained within a lead body 35. Each electrode is in communication with the stimulator/controller 12 (see FIG. 1*a*) via lead cable 34 (see FIG. 1*a*). By providing each lead 36(*a-b*) with multiple electrodes (or poles) 38 ensures that at least one pair of electrodes will lie close to and cross the phrenic nerve 42 which from here on will be referred to as traverse to the nerve in the manner shown in FIGS. 3-6 at all times after the lead is inserted or subsequently repositioned due to neck motion or repositioning of the patient (patients are routinely repositioning in the ICU to prevent bedsores). By placing the leads 36 transverse to the nerve 42 a pair of stimulation poles 38 can be selected to recapture the nerve 42 if necessary without requiring further physical manipulation of the lead 36 after insertion, thereby reducing the potential for infection and improving device usability. Put another way: the spacing of electrodes 38 along the lead 36 ensures that electrical communication between the lead 36 and the phrenic nerve 42 is maintained by allowing any of the four pole to be energized. Four poles were chosen based upon minimizing cost and complexity of the electronics but the design will also work just as well with 5, 6, 7 etc. poles. Thus, even if the position of the lead 36 has shifted as a result of patient movement or other factors two of the four poles 38 will always be in sufficient proximity to the phrenic nerve 42 to allow for stimulation to occur. Any combination of leads, surface area, distance between electrodes and lead diameter can be envisage that would optimize the stimulation ability of the lead to excite the phrenic nerve.

It is expected that a single pair electrode sites will be closest to the phrenic nerve and that the pair of sites that best stimulates the nerve will be found experimentally in each instance. Both unipolar and bipolar stimulation regimes are contemplated with both anodal and cathode stimulation available for the therapeutic use. Both monophasic and biphasic stimulation are contemplated but it is expected that biphasic stimulation from a single pair of well-placed electrode poles will be optimal and result optimal stimulation and minimal nerve damage. Charge densities greater than 30 $\mu C/(cm^2$ phase) have been shown to cause nerve and tissue damage and software and hardware protection mechanisms are envisaged to ensure this limit is not exceeded.

Given a number of different leads and stimulation devices may be attached, the lead 36 is given a specific resistor value (selection resistor) accurate to 5% or less to identify the lead to the S/C. The more accurate the selection resistor used the greater the number of leads that can be distinguished. For the purpose of giving an example a 1% accurate resistor will be used. Such resistors are commercially available and very low cost. The resistor is used to identify the lead type attached in terms of the number of electrodes available, the electrode surface area and may be used by software and hardware to limit the charge density based upon lead surface area. This allows the software and hardware to ensure the charge density for the attached electrode is not exceeded and minimized the potential for user error.

Figure 2A:
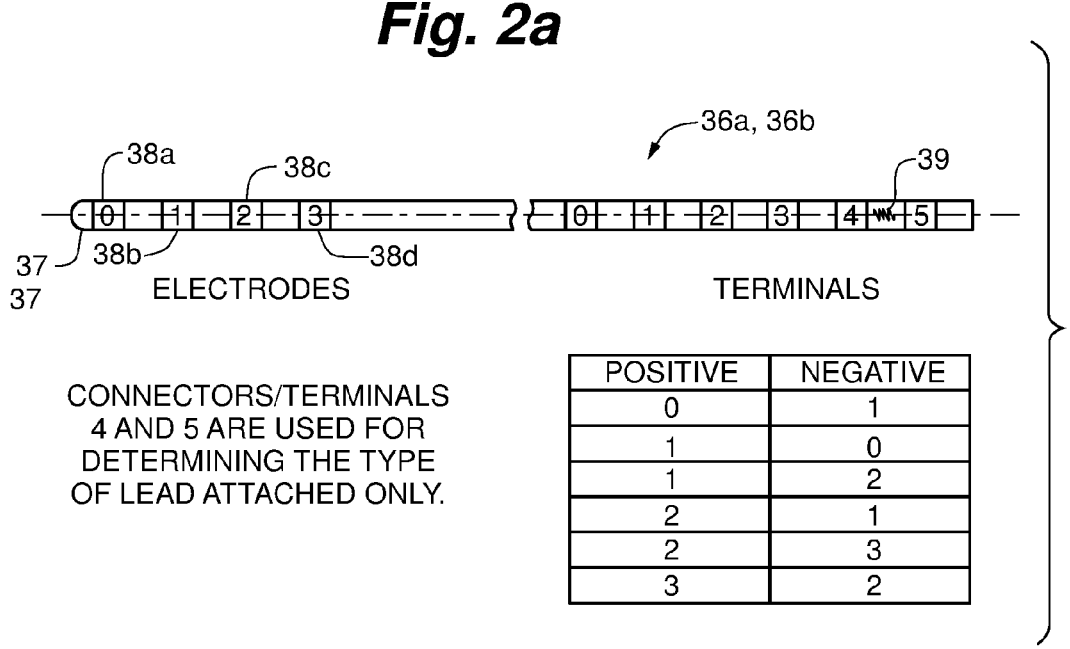

As is shown in FIG. 2*a*, the resistor 39 may be embedded into the lead 36 and can be read after connection. In a similar fashion a resistor may be associated with each electrode in the lead or associated with each electrode pair in the lead to provide location information to the S/C. The benefit of using a separate pair of connector terminals for measuring the resistance defining the lead type attached is that the resistance can be measured independent of any errors created by immersions of the in fluids or body tissue. Each resistor value must be distinguishable for all other resistor values used in other leads such that the values do not overlap in terms of the resultant measurement accuracy and is used to determine which probe is attached. Overlap between two distinct resistors values in terms of measurement range would cause confusion in the distinction between leads. To avoid potential issues with misreading the lead type attached, the measurement accuracy must be significantly less than the difference between the upper and lower ranges of the two closest resistor values. This difference should be large or the measurement accuracy must be high.

Figure 2B:
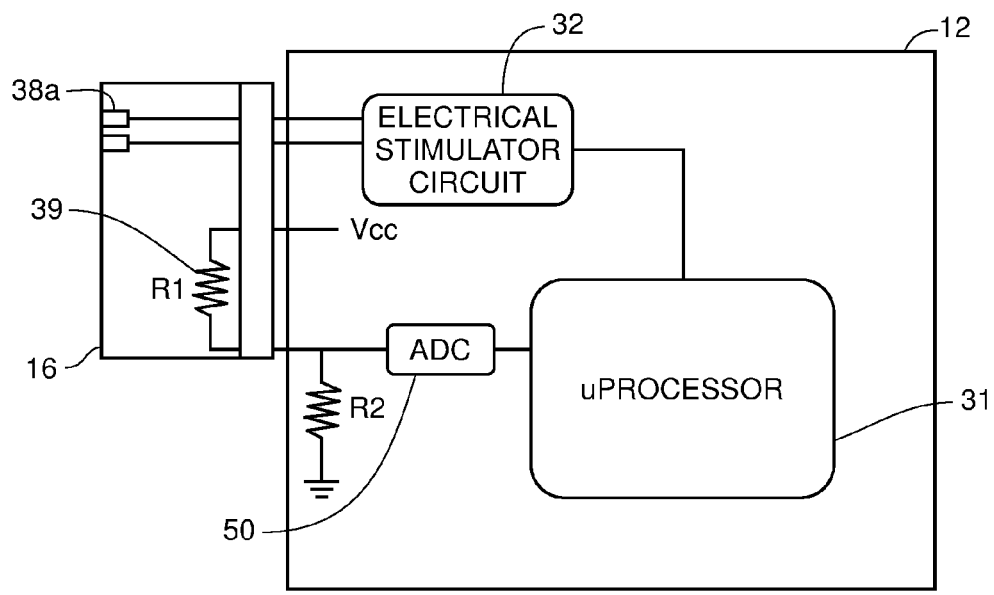

FIG. 2*b* shows how the selection resistor 39 could be used to determine which electrode is active. In this example Vcc drops across the resistor divider R1 and R2 and is measured by an ADC (Analog to Digital Convertor) 50 at the junction of R1 and R2. This example is given for illustration purposes only and in reality ESD protection and current limiting resistors would be used to prevent damage to the stimulator during use. For instance, R2 could be embedded within the lead and R1 could be internalized.

With a 1% accurate resistor, using a resistor divider with the required ESD protection, this system could easily accommodate 10 different configurations of electrodes without any potential for lead recognition error and accurately identify the electrode attached with a 10 bit or greater ADC (1024 bits). Assuming the R2=10K and R1 has a range of 1K to 500K and Vcc the input voltage is 5 volts, then range would be quite linear between 0.5 and 3.0 volts. The actual resistance values for R1 and R2 can be optimized based upon the actual system requirements. Look up tables with allowable voltages drop variances could be used to determine which lead type is attached. If the voltage is between x and y them probe z is attached.

The voltage variance is a function of supply voltage variation, resistor variation, electrical noise, ADC error etc. One skilled in the art of worst case error estimation can easily account for these potential variations using a worst case analysis or independently measuring the supply voltage and accounting for this error.

Other methodologies using resistors in conjunction with 4 or more comparator circuits (one more than the number of circuits required to be distinguished) could also be used to produce a digital output which would go high or low to denote which lead was connected but this would be less flexible and cost more. Other approaches such as using embedded RF ID tags within the lead are also possible but these typically cost much more and are subject to proximity issues, plus the detection of switching leads and making this detection becomes more problematic. A serial memory device using an I2C interface could also be used where a serial number denoting the specific lead attached along with pertinent parameters eliminating the need to update software if new leads are added to the product portfolio. Such a system while beneficial is complicated with the requirements of ESD protection. The benefit of the resistor approach is new probes can be added robustly, cheaply and distinguished by the system without the requirement for adding active components to the lead.

Another approach would be to use a serial memory device such as a Serial Electrically Erasable and Programmable Read-Only Memory (EEPROM) organized as 128 words of 8 bits each. Each EEPROM could be programmed with its own unique identification number and could also be programmed with the allowable setting limits or product specific features such as electrode surface area and number of electrodes. The EEPROM could also be used to store current settings. Thus, if a new stimulator was connected to a lead or the leads were switched on an existing stimulator, the stimulator device would automatically recognize the lead was changed after reading the data in the EEPROM and update delivered stimulus parameters in accordance with those data stored, such as in the form of a lookup table, etc. within the stimulator/controller 12 and accessible by CPU 31. Separate resistor values could also be used to distinguish left and right stimulation leads eliminating the requirement for the user to know which connector to attach to which lead. This is of particular issue in the ICU and eliminating the requirement for tracing leads after initial setup and disconnection would also reduce the potential for user misuse. Attributing a set of parameters to a specific lead would only be done after setup. After setup, the set of parameters attributed to a specified resistance would follow the specific resistance measured. The use of such resistance can also be used to define which functions in software to provide. For instance, specific leads used only during setup can be used to minimize functionality based upon the recognition of the measured resistance denotes that a setup lead is being used and that therapy functions would be disabled for this lead.

Figure 2C:
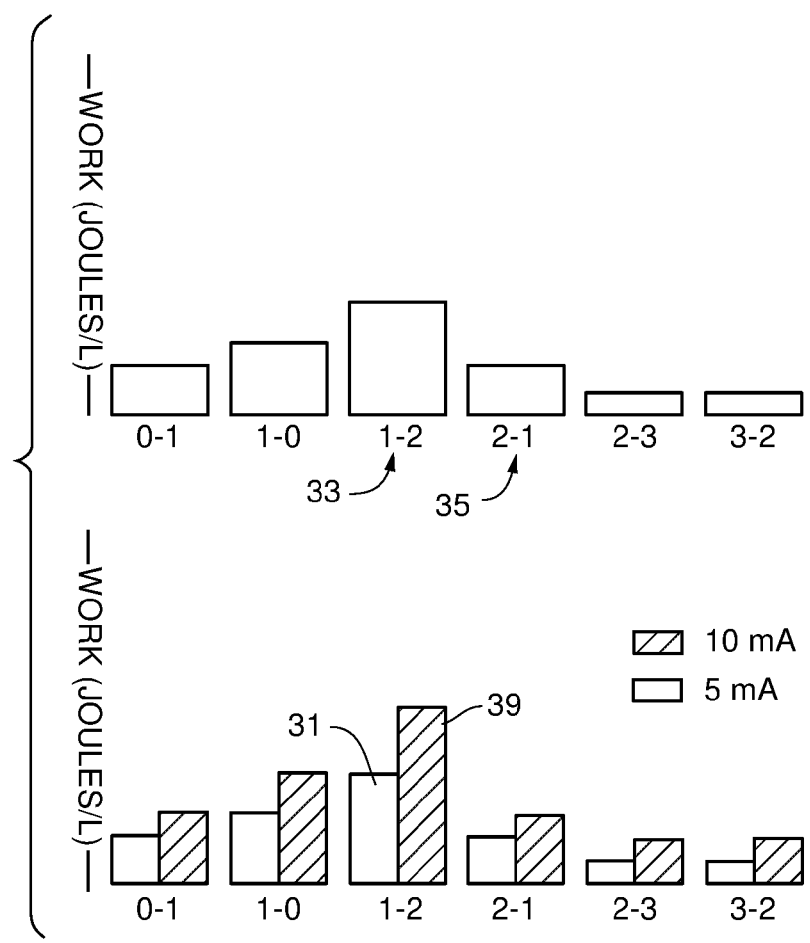
FIG. 2c is a chart comparing work with applied stimulation.

Based on the above description is should be understood that the system 10 functions by sending an electrical pulse via the pulse generator 32 as determined by established values determined by the system or input by a user to the CPU 31—to the leads 36 (via lead cables 34) so as to stimulate the phrenic nerve of a patient 22 in manner sufficient to activate the musculature associated with lung function (either or both sides of the diaphragm 20). The level of stimulation will occur within bounded values of a stimulation waveform in terms of current, current densities, charge densities and voltage as determined by the stimulator/controller 12, CPU 31, etc. In FIG. 2c the electrode couplet 1-2 at location provides more work by the patient than electrode couplet 2-1 seen at location 35. This is generally true but some level of proportionality appears with current levels supplied to the lead. As seen at location 39 and 31.

The stimulation may be to both the left and right phrenic nerve and thus be bilateral or unilateral, while the resultant effect of stimulation on the diaphragm may be bilateral or unilateral as well.

In some embodiments a purpose of the stimulation regime is to cause sufficient activation of the muscle to cause a training effect on the musculature. Muscular train at level sub maximal are believed to provide a therapeutic benefit and to aid in weaning patients from mechanical ventilation more quickly than is otherwise possible. Effectiveness of the level of any given stimulus will be determined by observed patient work in a sedated patient whose respiratory function is partially or entirely supplanted by mechanical ventilation.

The level of muscle activation required to induce the desired training effect may be below the level required for gross motion of the diaphragm and lungs in a normal healthy patient. When a patient has abnormal respiratory mechanics the work required may be significantly higher for that patient than a healthy person. For this reason, medical judgment will be required to target a work or power expenditure suitable for the therapy. It is expected that the physician will target a nominal work or Work-of-Breathing (WOB) value that is in the range of expected power for a healthy normal patient. This work or power level will be a reference point and used to titrate the level of stimulation. It also possible once a target level of work is determined by the clinician, the stimulator could automatically increase the level of stimulation based upon a level of work desired based upon a feedback loop of work measured within bounds set by the clinician for a maximum allowable current amplitude, frequency of stimulation etc.

The periodicity of the electrical stimulation may vary over a wide range and it may be delivered in synchrony with natural ventilation.

However, before any such stimulation may occur, the phrenic nerve (right and/or left) of the patient 22 must first be located and accessed.

Turning now to the insertion of the lead 36 may be accomplished by a variety of techniques, an example of one being shown in the sequence of images depicted in FIGS. 7-10.

Before lead insertion, the patient 22 is intubated and sedated, or more likely already in this state due to the presumption of requiring mechanical ventilation. The patient is in supine position (lying flat) with head turned to the contralateral side.

Identification/location of the phrenic nerve is performed using a handheld stimulator 44 and ultrasonic probe at the level of the cricoid cartilage and lateral of border of the sternocleidomastoid muscle (SCM) approximately at the level of the C5 vertebra such as in the manner shown in FIG. 7. The patient is first assessed to determine suitability for lead insertion. Ultrasound is used to determine the patient anatomy is suitable for lead placement and the hand held stimulator is used to determine that the phrenic nerve is functional and capable of stimulating the diaphragm. Once the patient has been accessed as suitable for treatment, the lead insertion site identified, the area around it is cleaned and sterilized. A small incision 46 is made at the designated access site with a scalpel or other cutting instrument.

Figure 1B:
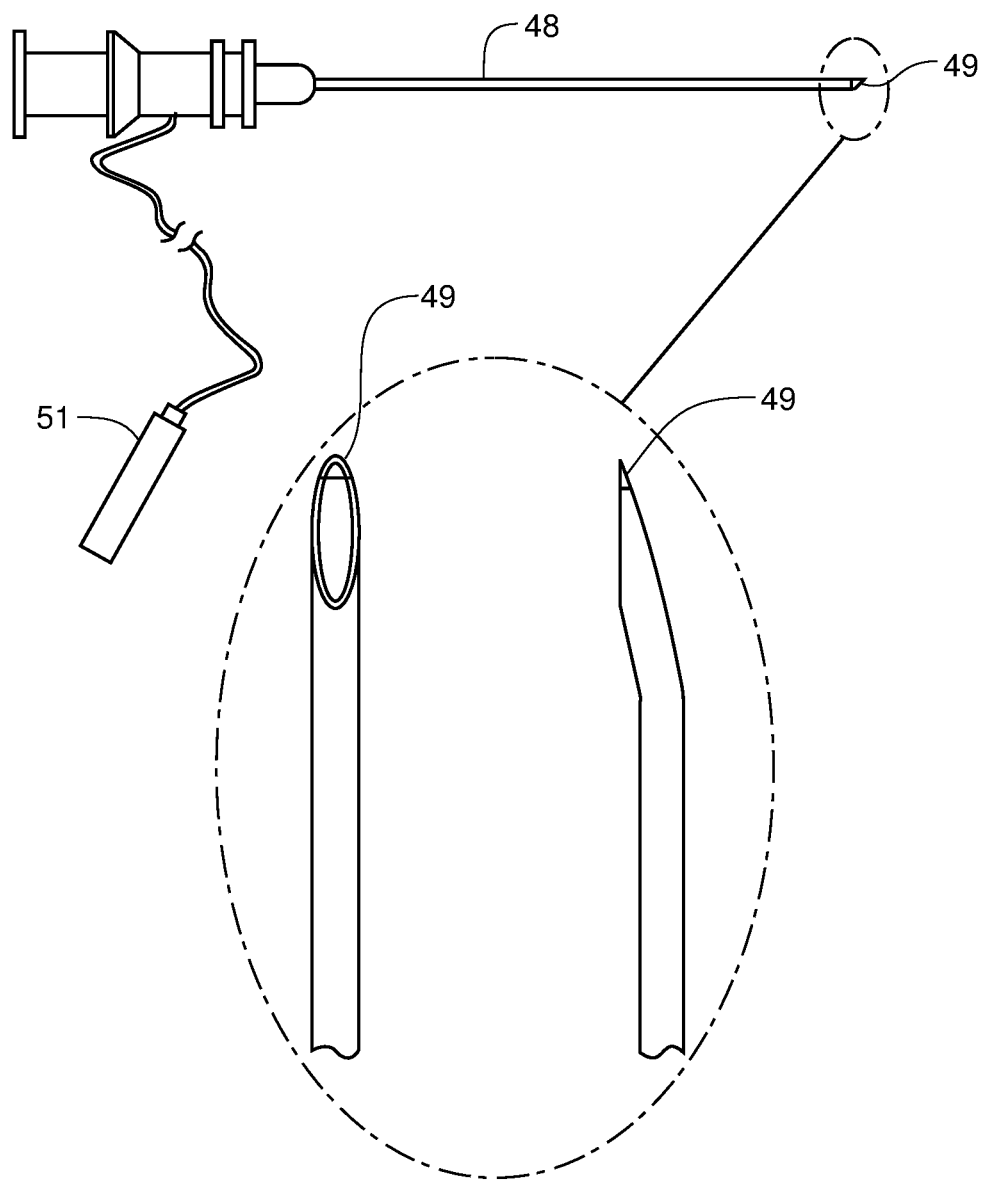
FIG. 1b is a view of an embodiment of the insertion needle used in initial phrenic nerve location.

With ultrasound guidance, a cannula 48, such as a Pajunk® Touhy needle shown in FIG. 1b, is inserted into the initial incision site. The Touhy needle is a monopolar needle with an insulated shaft with only the tip 49 being electrically conductive and in communication with the stimulator/controller 12. This allows for localized nerve stimulation at the tip 49. The needle 48 is attached to the stimulator 12 via an extension lead 51. A second electrode 53, shown in FIG. 7, is connected to the patient's skin and to the extension lead to create a return path for the electrical stimulus. This extension lead 51 contains a resistor that identifies that the setup needle 48 is attached and that the needle insertion process is underway. The user is now given the ability to stimulate the needle 48 via the stimulator/controller 12. The software (not shown but should be considered a component of the CPU 31 shown in FIG. 1a) in the stimulator recognizing the unique resistance of the extension lead 51 for the monopolar needle 48 switches to a nerve finding programs which differs from the e pacing function discussed in greater detail below.

Once the needle 48 is advanced beyond the skin insertion site, the needle is advanced parallel to the muscle fibers of the anterior scalene muscle (ASM), and under the sternocleidomastoid muscle (SCM) (illustrated in FIG. 3) with the tip of the needle 48 just distal to the phrenic nerve 42. Stimulation can be used to induce a hiccup like action of the diaphragm and let the operator know that they have identified the correct nerve under ultrasound guidance. This stimulation can be limited to being performed during inspiration period utilizing the flow sensor to distinguish between inspiration and expiration such that diaphragm contraction is in synchrony with the breath phase of the ventilator. This prevents auto-triggers on the ventilator and minimizes the potential for barotrauma and auto PEEP.

Note that if at any time collateral e.g. brachial stimulation is observed (as noted by corresponding arm movement with stimulation) then the cannula 48 is repositioned approximately 1 cm caudally. The stimulation process is then repeated at the new location until corresponding diaphragmatic movement is noted without collateral stimulation.

Figure 3:
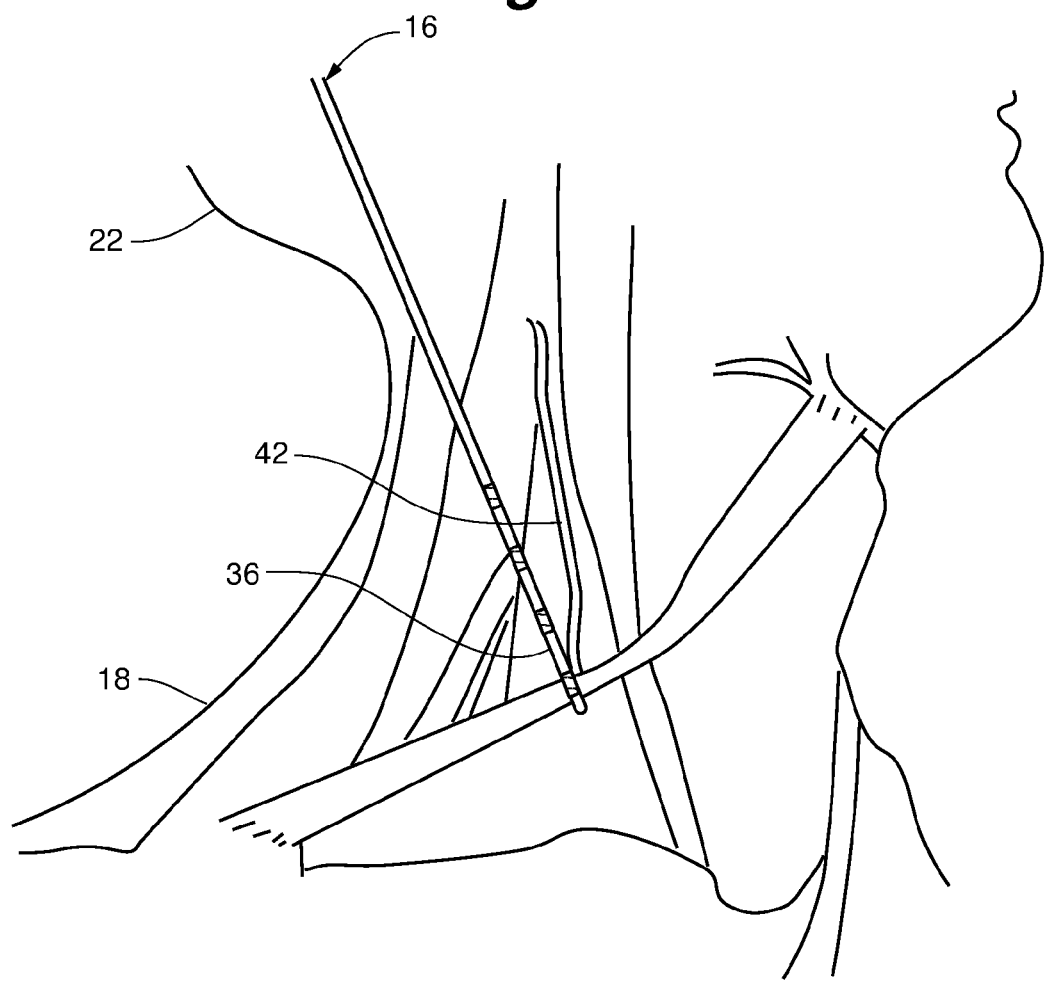
FIG. 3 is a close up sectional anatomic view of the patient's neck shown in FIG. 1 with additional anatomy dissected to the proper positioning of a lead relative thereto.
Figure 4:
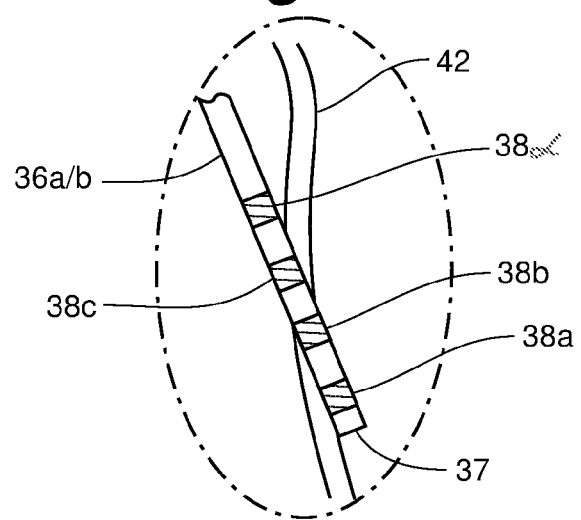
FIG. 4 is a detailed but schematic view of the lead shown in FIG. 3 depicting the proximity of individual electrodes to the phrenic nerve body.

Once signal capture is achieved the needle is advanced to transverse the phrenic nerve 42 under ultrasound guidance such as in the manner shown in FIGS. 7-8. A multipolar lead 36 is inserted through the monopolar needle 48, such as in the manner shown in FIG. 8. The position of the lead tip 37 (see FIG. 2*a*) is observed by ultrasound and is positioned distal to the tip 49 of the cannula 48. Once the lead 36 is properly positioned (such as is shown in FIGS. 3-4), the cannula 48 is removed from the patient 22 in the manner shown in FIG. 10. The multipolar needle/lead 36 is designed such that both ends will fit through the monopolar needle 48 facilitating the needles removal. A stylet may be used to strengthen the lead during insertion into the needle.

The lead housing 35 may be flexible to maximize comfort and the axis of the lead 36 will form an angle with the axis of the body of the phrenic nerve 42. Both orthogonal alignment (an example of which is shown in FIG. 8) and substantially parallel alignments (an example of which is shown in FIG. 9) are contemplated with the included angle varying from about 90 degrees to 0 degrees.

Next the lead 36 is connected to the handheld stimulator 44 and diaphragmatic movement is verified. There are six possible combinations to tests as outlined in FIG. 2*a*. The operator uses the default stimulation parameters provided by the stimulator/controller 12. Stimulation will be delivered in synchrony with the inspiratory cycle of the ventilator at the operator's request. The operator may quickly go through the combination of stimulation poles by testing the various combinations over a number of breaths. This could be shown graphically to the operator in terms of work for a given electrode pair similar in a bar chart form making the distinction of best pair easy for the operator. The level of work induced by the stimulator may be averaged over a number of breaths. Stimulation parameters may also be increased if diaphragm movement is not seen or measured. As stimulation parameters are adjusted this could also be shown graphically by adding bars to the bar chart for the specific pair allow the operator to see the difference. The measurement of WOB, which is described below, is critical to finding the optimum pair of poles for stimulation. If movement cannot be verified in terms of patient WOB during electrical stimulation, then the procedure is terminated.

Assuming however that the process is successful and diaphragmatic movement is confirmed, the process is repeated on the contralateral side to thereby implant a lead 36 at both the right side and left side phrenic nerve.

It should be recognized by one of ordinary skill, that the above process provides notable benefit in that this technique avoids any inadvertent vascular-neuro-pulmonary injury that more invasive surgical techniques or implanted devices may cause.

In addition, lead 36 is free to move along the insertion path if the patient 22 is repositioned. Since such movements will be initiated by the clinician, adjustments to optimal stimulation pairs can be performed if the clinician recognizes a reduction in the work of breathing (discussed in greater detail below) after a positional change. Also, and as mentioned above, the primary purpose for using multiple poles in each lead 36 ensures that at least one electrode pair will still cross the phrenic nerve before and after any repositioning of the patient.

System Operation Description with the Lead

With the lead structure and the technique for locating and accessing the phrenic nerve of the patient well described we turn to the operation of the electrode selection methodology. Lead insertion results in the axis of the lead body lying across the nerve bundle of the phrenic nerve, such as in the manner shown in FIGS. 3-6. A pair of the electrodes will lie closest to the phrenic nerve 42 and the stimulator/controller 12 finds that pair by stimulating sequential pairs of electrodes (two of electrodes 38*a-e*) during selected breaths while looking at the work or power generated by that breath as measured from the pressure history at the wye sensor 14. In general, the maximal work for the minimal stimulation current will correspond to the best electrode pair. This process can occur automatically or directed by the user physician/technician (not shown). The level of work or power for each stimulus pair may be assessed over a number of breaths and compared to that exerted by the other pairs of poles. The maximum respiratory power measured for a given level of stimulation of the pair of poles would then represent the optimal pair. Since the lead 36 is not firmly anchored it can move and the best electrode pair may change with time or repositioning of the patient. This process for searching for the optimal pair may be initiated upon request by the operator or could be initiated automatically based upon a level of the patient work dropping below a specific level. See for example the change in lead positions depicted in FIGS. 5 and 6. In FIG. 5 the lead as inserted may have moved or been misaligned relative to the phrenic nerve due a patient positional change but given the flexibility of selecting the lead stimulation poles 36 and the system 10 the clinician may easily adjust the lead stimulation poles. This change in optimal poles is illustrated in FIG. 6 where the optimal poles change from 1 to 2 to 0 to 1

Stimulation optimization will likewise compare the work or power of a breath as a proxy for evoked response of the diaphragm. The stimulation may occur at any parameter set within bounds defined by the input parameters on the GUI 33. In general, the clinical user will look for stimulation parameters within these limits that maximize work or power measured for the breath.

It is anticipated that the GUI 33 will have one control for stimulation level with detailed parameters set a priori and a display of work/power of the stimulated breath. The user will exercise medical judgment in setting stimulus for a given observed work/power of the stimulated breath.

System Operation Description with the Wye

As described in connection with FIG. 1a the pulse generator 32 within the stimulator/controller 12 delivers electrical stimulation to at least two electrodes or a pair of electrodes (two of electrodes 38a-e) selected from all available electrodes on lead 36. One of the electrode pair is the cathode and the other electrode is the anode for bipolar stimulation. This bipolar stimulation is one embodiment. It should be understood that unipolar stimulation with a remote indifferent electrode is also contemplated within the scope of the invention. The electrical stimulus will have at a minimum an adjustable number of breaths between stimulation breaths, repetition rate, a current amplitude, a pulse width, and a pulse train waveform. The values of these parameters may be set by the user through interaction with the GUI interface 33 of stimulator/controller 12 separately for both pacing leads. These electrical parameters may vary over a range and it is expected that many or most will be set automatically as set forth below. Other input parameters required for system operation are patient lung compliance and a patient lung resistance. These can be measured by the ventilator or using the stimulator and entered by the user via GUI interface 33. FIG. 19 is a table showing the parameters for the GUI and the set labeled 900 will be input parameters (13 on FIG. 1a) that will set by the user. The parameter space labeled 902 in FIG. 19 is expected to be displayed on the interface 33 screen. The parameters 904 will be input by the user as well as these are required for the work and power measurement process. These are typically measured by modern mechanical ventilators and may be entered from there. These values can also be estimated from knowledge of the patient and their state of health.

Figure 18:
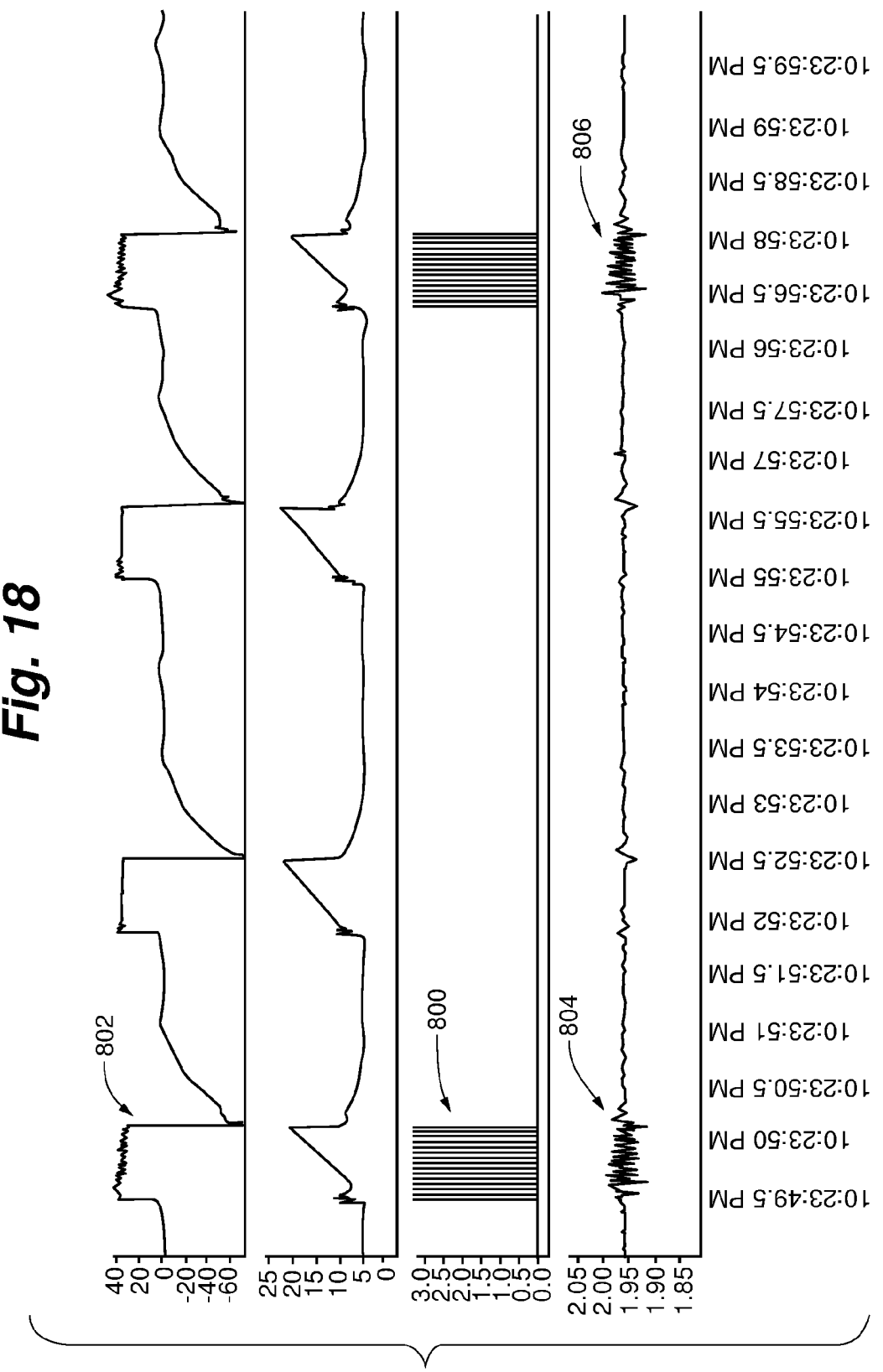
FIG. 18 is a presentation of animal data in the form of waveforms measured during periodic stimulation of a sedated pig.

In operation, the stimulator/controller 12 will count patient breaths based on wye pressure and wye flow communicated via sensor cable 28 from the instrumented wye (wye sensor) 14 to the stimulator/controller 12. Although the stimulator/controller can be set to interact with each and every breath, it will normally select a single breath from a sequence of breaths herein after referred to as the selected breath. A simple ratio is used and in the various figures both a one of two (1:2) and a one of many ratio (1:N) are shown for the selection criteria. The selection criteria mean that both the following or subsequent breath will be mechanical ventilator controlled and the preceding or predecessor breath will be mechanical ventilator controlled. The immediately preceding bread is hereinafter referred to as the predecessor breath while the immediately succeeding breath after a stimulated selected breath is called a successor or subsequent breath. When referring to either of these two breath types the term "companion breath" is used. The animal data presented in FIG. 18 shows a 1:3 stimulation regime and this animal work suggests that a ratio of 1:2 to 1:8 may encompass a workable therapeutic range for a human patient.

The human breath has an inspiratory phase characterized by a positive flow of air through the wye into the patient, and an exhalation phase which begins when wye flow drops below zero and turns negative as the patient exhales the volume just inspired. This end inspiratory event begins the outflow portion of the breath cycle. In operation, the stimulator will deliver the electrical stimulation starting with the inspiratory phase when flow exceeds a predetermined level and end stimulation at the start of the exhalation phase when flow drops below a predetermined level, this stimulus will occur only during the selected breath. Since the stimulation is not continuous for each inspiration there will typically be a predecessor mechanical ventilator breath and a subsequent breath. The selection of a breath is a simple ratio. That is selected breaths may occur every other breath (1:2) to any arbitrary value say one selected breath every 20 breaths (1:20). It is expected that a ratio of 1:4 or so will provide adequate treatment for VIDD however this will need to selected based upon clinical practice.

The work and power measurements are made based upon the respiratory equation of motion. Although unnecessary for a qualitative indication of work or power it is best to convert measurements to a uniform standard and the patient work level or power expended in a breath is reported as the Work-of Breathing (WOB). This convention reduces the necessity to convert units and the like. The equation of motion used to calculate WOB is the same equation used to set the target pressure level based upon the proposed level of support in Proportional Assist ventilation (PAV) mode of ventilation, which is a spontaneous mode of ventilation. The ventilator may be used to assess the patient's compliance and resistance because it dictates when respiratory mechanics maneuver can be initiated and the resultant compliance and resistance measurement values will then be used to determine the WOB for the patient. The user will need to transfer the ventilator measured compliance and resistance measurements manually from the ventilator to the PEPNS console. It will be necessary to perform respiratory mechanics periodically but unlike PAV, the potential for runaway does not exist. In theory if the patient does not make a voluntary inspiratory effort during a mandatory breath or the PEPNS System does not electrically stimulate the diaphragm, the WOB should be zero joules/L. Work is normally measured in Joules but dividing by the volume allows the level of work to be normalized against a unit volume. The equation of motion equation should predict the wye pressure accurately and when the measured wye pressure matches the predicted wye pressure it indicates that there is no patient effort and thus no WOB. A difference will occur in the predicted and measured wye when the diaphragm is stimulated and these will be attributed to diaphragm effort.

The benefit of this approach is that the WOB can be assessed in relation to the level of work a normal healthy patient exerts during breathing at rest. Normal WOB has been reported in the literature to be 0.3 to 0.5 J/L in healthy children, adolescents, and young adults. Certain disease states that increase lung resistance and compliance dramatically increase the level of work a patient has to exert to breath so basing the level of work on a pseudo WOB measurement such as a reduction in the pressure time product (PTP) could mean that a sick patient is working at significantly higher levels than a normal healthy person at rest. Using PTP as a proxy for work is not workable in a clinical setting as it may greatly overestimate or underestimate patient work resulting in extremely inappropriate stimulation levels. This is not the purpose of the PEPNS system (over exertion of the diaphragm) a method to assess and prevent this from occurring is disclosed. Allowing the clinician to adjust the stimulation level based upon a known measurement of WOB allows the physician to titrate the level of effort based upon clinical assessment. Feedback does not exist to set this desired level of WOB, this is the physicians decision based upon a myriad of inputs that will be unknown to the stimulation device, disease state, age, weight, temperature, heart rate, end tidal CO2, metabolic rate etc. Once a level has been set by the clinician feedback could be used to maintain the desired level. Use of this WOB measurement will help minimize the potential for inducing diaphragm fatigue due to overstimulation which could happen when blindly setting a stimulation level without understanding the underlying respiratory mechanics and level of work being induced. Examining diaphragm motion is like looking at a machine lifting a weight. Knowing the acceleration or velocity of the weight gives no idea of how much work the machine is performing. Knowledge of the weight is required and this is comparable to knowing the patient's compliance and resistance.

The equation of motion for respiration will be used to estimate the patient WOB in an electrically stimulated breath. In a breath without electrical stimulation the WOB should be 0 J/L because $P_{mus}$ will be 0 cmH$_2$O.

According to the equation of motion for the respiratory system:

$$P_{vent}+P_{mus}=\text{elastance}\times\text{volume}+\text{resistance}\times\text{flow}$$

Where elastance a measure of the tendency of a hollow organ to recoil toward its original dimensions upon removal of a distending or compressing force. It is the reciprocal of compliance. Resistance or Airway resistance is the opposition to flow caused by the forces of friction. It is defined as the ratio of driving pressure to the rate of air flow.

Elastance is measured in cmH$_2$O/Liter, volume in Liters, resistance in cmH$_2$O/Lpm and flow in Lpm. $P_{vent}$ is the pressure exerted by the ventilator and $P_{mu}$ is pressure exerted by the diaphragm muscles and both are measured in cmH$_2$O.

This equation can be rearranged to show:

$$P_{vent}+P_{mus}=\text{elastance}\times\text{volume}+\text{resistance}\times\text{flow}+PEEP$$

$$P_{mus}=\text{elastance}\times\text{volume}+\text{resistance}\times\text{flow}+PEEP-P_{vent}$$

Where $P_{vent}=P_{wye}$

Work=Pressure×Volume

Work=$\int_0^{Vt} Pmuscles * dV$ (joule)

Where dV is the rate of change of volume and Vt is the tidal volume of the inspiration. This can also be expressed as:

Work=$\int_{t0}^{t1} Pmuscles * Qdt$

Where Q is the instantaneous flow, $t_0$ and $t_1$ are the start and end of inspiration.

WOB=Work/Liter=Work/Vt (joule/Liter)

Most ICU ventilators are capable of measuring respiratory mechanics properties such as static and dynamic compliance and resistance. Since the WOB will be primarily used to gain an understanding of the level of effort that electrical stimulation is creating small errors in measurements will not be of consequence unlike the accuracy requirements needed for compliance and resistance measurements needed for modes of ventilation such as Proportional Assist Ventilation. In use the physician user will input measured or estimated lung compliance and lung resistance measures in to the GUI. It is also possible with the sensors at the wye, the wye flow and pressure to assess the patient's respiratory mechanics. Currently for simplicity these measurements will be made independently but they the PEPNS system is capable of making these measurements during ventilation.

The flow sensor and wye pressure sensors can be used to measure Pvent (Pwye) and flow at the wye, Qwye directly. Volume accumulation may be calculated by integrating the Qwye as the breath progress beginning at the start of inspiration and ceasing at the end of inspiration.

The Operator can enter values for compliance and resistance into the stimulation device via the GUI and update these values when they have been deemed to change significantly. The stimulation device could also communicate directly with the ventilator and eliminate the need for this data entry and get the values directly from the ventilator.

The benefit of this method of calculation for work is no data on previous breaths or breath types is required. The measurement in independent of the previous breath type and no knowledge of the previous and current breath are required. In contrast PTP as a pseudo measurement of WOB will only work if the same breath type are compared between a stimulated and unstimulated breath.

Turning to FIG. 11, there is shown a set of waveforms with the same time scale 108. A flow channel 100 is shown with the simultaneous signal of the pressure channel 102. Both the pressure and flow measurements reflect the values at the wye 14 and these are reported to the stimulator/controller and form the wye pressure measurement and wye flow measurement referred to later in the description. Also seen in the figure is a waveform panel 104 showing the electrical stimulation supplied to lead system 116 from the pulse generator 32. A calculated value 122 is shown as the waveform 106 and it is labeled work in the figure but it reflects both observed work as well as power delivered by the patient into the system, as explained in detail later.

In FIG. 11 the selected and stimulated breath generally designated 110 commences at time T=1 with an inspiratory phase indicated by the rapid rise in flow at 114. This is a flow control breath denoted by a constant flow and the resulting pressure being a function of the compliance, resistance and diaphragm effort of the patient. This inspiratory flow starts the delivery of the stimulus at 116 in the figure. When the patient's exhalation begins at 118 the stimulation ends at point 120. During the inspiration duration from event 114 to event 118 the pressure in the wye is compared with a predicted and modeled pressure in the wye. This pressure difference is called Pmus and it reflects the pressure component of the work done by the patient's muscle. Pmus along with other parameters is used to compute the value of work and power seen in channel 106 as work/power waveform 122. Basically the wave form envelope is the instantaneous work performed and the area bounded by the waveform 122 is the power expended by the patient 22.

Turning to the previous or predecessor breath 112 we see a another mechanical ventilator breath in a flow control mode. At time T=0 the breath starts and the patient experiences a rapid delivery of flow symbolized at infection point 124. The pressure rise is set by the mechanical ventilator and is represented in the figure as slope 126. Since this is not a stimulated breath the Stim Signal channel is empty and since the predicted value of Pmus and the measured value at the wye are identical they add to zero and this term in the work/power expression is zero so the work value computes to zero and nothing or no work is shown in the work channel 106.

FIG. 12 follows the same format as FIG. 11 but in the interest of clarity the timing synchrony lines are not shown. In this breath sequence a predecessor breath 200 is followed by a selected stimulated breath 202. The pressure controlled breath 200 begins at time T=0 with the rapid pressurization to the plateau 208. This corresponds in the flow channel 206 with the rapid rise in flow at event 210. At time T=1 the mechanical ventilator has met its inspiratory time requirements and the pressure drops and the flow goes negative as the inspiratory phase ends and the expiratory phase begins. After the mandatory breath period expires the ventilator delivers another mandatory breath and the inspiratory flow detected at the wye 24 causes the console to turn on stimulation seen as stimulation train 212. In this pressure controlled breath the pressure level is also set to the same pressure level and both breath 200 and 202 have reached the preset pressure shortly after T=0 for breath 200 and shortly after T=3 in breath 202. During the second mandatory breath 202 the stimulation causes work of the patient which increased the flow into the lungs as seen by comparing height 214 with 216 in the figure. The pressure remains constant between because these are pressure controlled breath. If Pressure Time Product (PTP) methodology was used as a method of determining WOB there would be no difference in work measured yet the effect of stimulus can be seen in the differences between resultant flow. The conventional PTP proxy is blind to obvious increase in patient work while the inventive and disclosed methodology shows an accurate measure of work at waveform 218. This point is shown on the figure by the lack of a work waveform at location 220 corresponding to time T=0 on the figure.

FIG. 13 shows the operation of the invention in the context of a more complicated Synchronized Intermittent Mandatory Ventilation (SIMV) mode in a flow control regime. SIMV is used as a transition mode where the clinician is able to set a minimum number of breaths per minute and addition breaths taken by the patient will result in a spontaneous breath being delivered. The most common form of a spontaneous breath is pressure support ventilation which is both initiated and terminated by the patient. The mandatory breaths may be ventilator initiated or patient initiated. There are four breaths in the FIGS. 300, 302,304 and 306. The first breath 300 is initiated by the mechanical ventilator and shows a flow control breath, similar to 112 in FIG. 11. It precedes the second breath 302 which a spontaneous breath. In this example breath 302 is a selected breath so it will invoke stimulation of the stimulation lead because the console will have no knowledge of the type of breath about to be delivered it is critical that the WOB measurement is independent of the breath type and any knowledge of the preceding breath types. This is also a patient initiated breath and in this case a spontaneous breath. The inspiration starts at the inflection point 308 in the flow channel 310 which starts the stimulation 318 in the stimulation channel 314. The pressure measurement from the Wye 14 is taken as the Pwye measurement which is used to calculate the presence of and the value of the work and power of the patient in breath 302 as a function of the difference between the measured and predicted wye pressure. In accord with the SIMV modality the next breath 304 will be a mandatory breath since in our example it is not a selected breath it will not be stimulated and it will be similar to breath 300. After some delay indicated by the line break in the channels another mandatory breath occurs in this example it is a selected breath and therefore a stimulated breath. In this breath, the machine initialed flow event at inflection point 320 starts the stimulation 322 in the stimulation channel 314. Once again, a work and power measurement can be made and displayed as seen by waveform 324 in the work channel 316.

It is important to note the predecessor breath 300 and the subsequent breath 304 are essentially identical except for their timing relationship to the selected breath 302 and 306, that is breath 304 is both subsequent to breath 302 and a predecessor breath to selected breath 306. For this reason, the un-selected predecessor breaths or subsequent breaths are called "companion breaths".

FIG. 13 also shows no measured work for the companion breath 300 at location 326 and no work for the companion breath 304 at location 328. While the selected stimulated breaths show patient work in the work channel at 324 and 330 respectively. The duration 332 of stimulation of selected breath 302 is initiated and terminated by the patient while the selected breath 306 is both initialed and terminated by the mechanical ventilator 30 resulting in differing waveforms for work as seen comparing work waveform 324 with work waveform 330. The figure shows the compatibility of the system with SIMV ventilation modalities.

Figure 14:
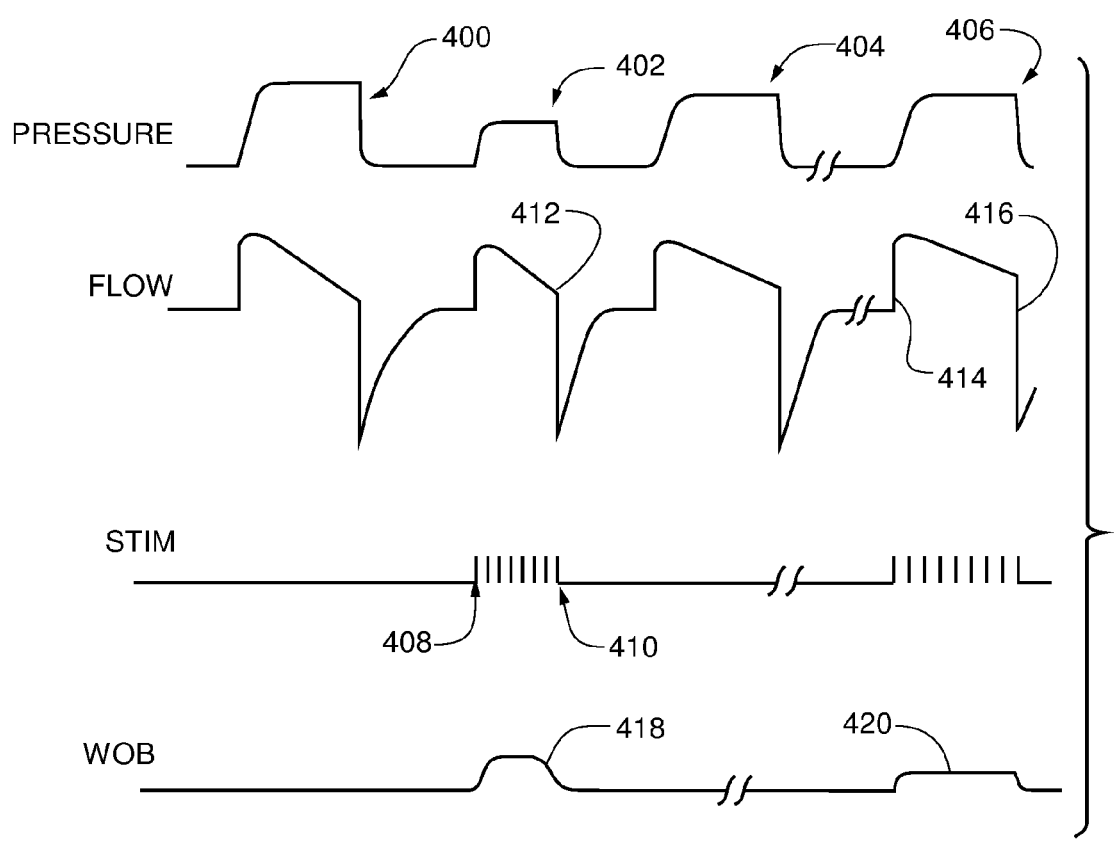

FIG. 14 shows the operation of the invention in the context of a more complicated Synchronized Intermittent Mandatory Ventilation (SIMV) with pressure control as the mandatory and pressure support ventilation (PSV) as the spontaneous mode. There are four breaths in the figure 400, 402, 404 and 406. Breath 400 is a mandatory breath and breath 402 is a spontaneous breath in PSV and it is a selected stimulation breath. In the figure the flow initiated stimulation begins at 408 and ends at 410. The duration of stimulation is patient driven and is the consequence of a patient initiated inspiratory phase and the cessation of stimulation is triggered by a patient initiated exhalation at point 412. After some time, a second selected breath occurs and it is a machine initiated mandatory breath with the beginning of stimulation at 414 and end of stimulation determined by the mechanical ventilator at location 416. In this case it was preceded by a PCV mandatory breath 404. Once again only the stimulated show an actual work measurement at locations 418 and 420 for selected breaths 402 and 406 respectively. In this example the system is integrated with pressure controlled and pressure supported modalities where pressure time product measurements will not work.

Figure 15:
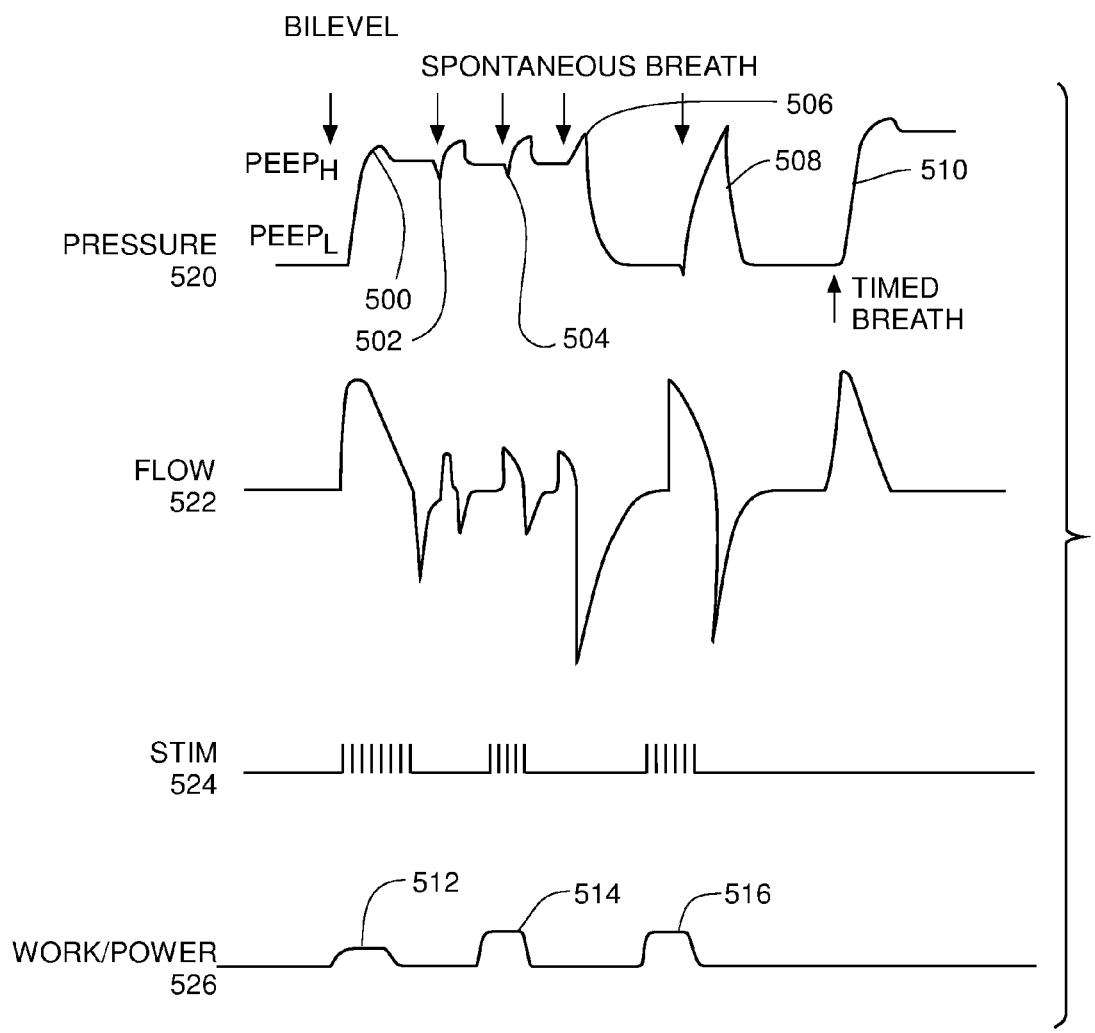

FIG. 15 shows the operation of the system in a bi-level ventilator treatment modality. In this mode two post expiry pressures PEEP hi and PEEP lo values are set on the mechanical ventilator 30. These may be tens of cmH20 apart in pressure. There are six breaths shown in the figure. Using a one in two ratio (1:2) for selecting breaths. Breath 500 breath 504 and breath 508 are selected stimulated breaths. While the predecessor or subsequent, companion breaths 502 and 508 are driven by the mechanical ventilator 30. Note that the system gives work measures at locations 512, 514, and 516 respectively for the selected breaths 500, 504 and 508. Note as well that the pressures and flows between these selected and stimulates breaths vary dramatically as represented by the corresponding waveforms in the pressure channel 520 and the flow channel 522. Using the work and power methodology relying on Pmus or the difference between predicted and measured wye pressure Work is calculated in a sensible way and the largely different pressure and flow traces are accommodated. An alternative Pressure and Time Product estimation of work is unable to provide reliable and accurate measure of work and power where the pressure at the wye is integrated and subtracted from the preceding wye pressure. As can be seen from the previous ventilator modalities in FIG. 11 to FIG. 15 the inspiratory time and breath type may vary significantly between breaths. It is general true that any estimation of work based upon a comparison of two breaths even if the breaths are of the same type is unworkable in many situations which can arise, and are exemplified by the FIG. 6 waveforms.

FIG. 16 shows the system operating in a pressure regulated volume ventilation modality where both pressure limits 608 and flow limits 610 are set for the mode by interaction with the mechanical ventilator 30. This figure shows a 1:2 selection ratio with breath 600 and 604 receiving stimulation, and companion breath 602 controlled by the ventilator This pressure regulated and volume regulation mode limits both pressure and flow as seen with breath 602 inspiration event 612 rapidly reaching the limit shown as 610. As well as reaching the pressure limit a short time later indicated by reference numeral 614. Even in this mode the work and power measurements seen at 618 and 616 respectively for selected breath 600 and selected breath 604. Once again there is no reported work the machine breath 602, even when the machine breath 602 is operating at limit conditions.

Work/Power Measurement

Figure 17A:
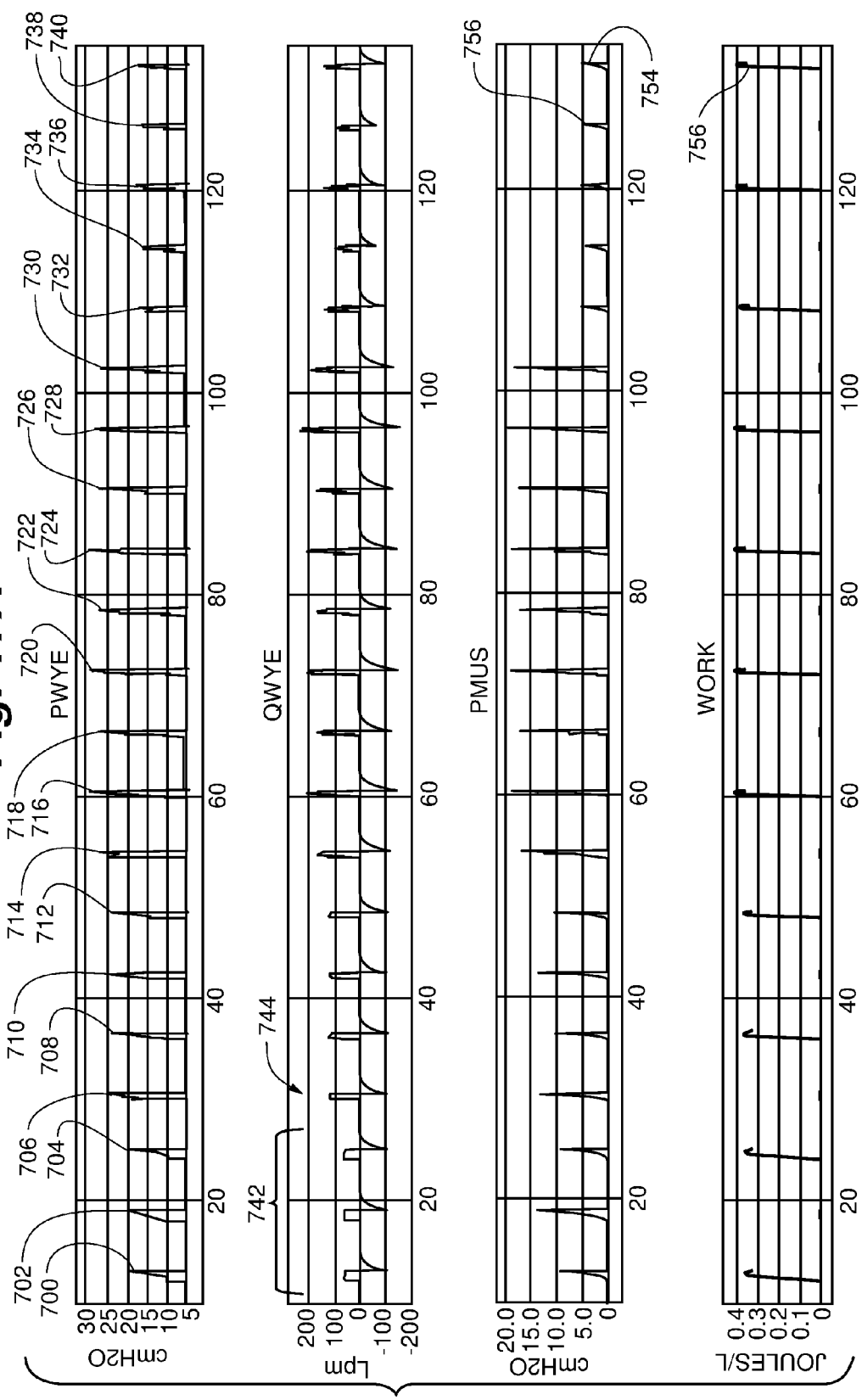
FIG. 17A depicts breathing waveforms and measurements of work using two different techniques.

FIG. 17 A and FIG. 17 B should be considered together. FIG. 17A is a diagram of a sequence of breaths that was generated by a computer model of a patient coupled to mechanical ventilator via a patient circuit tubing operating in a volume control mode and then in a pressure control mode. The numbered breaths 700,704,708,712,716,720,724, 728,732, 736,740 seen in the pressure channel 746 are all selected stimulated breaths with the selection criteria ratio being 1:2. The remaining companion breaths are predecessor or subsequent breath driven by the mechanical ventilator. Breath group 742 in the flow channel 748 are all volume controlled breaths VCV and the remaining group 744 in the flow channel 748 are all pressure controlled breaths.

The patient compliance and resistance were modeled to be 100 ml/cmH2O and 5 cmH2O/Lps respectively. The patient circuit tubing compliance was set to 2.5 ml/cmH2O.

Channel 750 represents the pressure time product of each breath. It is conventional to compare the pressure time product 754 of a breath say breath 740 with the pressure time product 756 of a predecessor breath say for example breath 738. In the table at breath 740 the pressure time product difference is −10. In conventional practice this value would be taken at the work of breath 740. However, we know this is a stimulated breath and the patient work is not negative. Work channel 752 using the previously described process the work 756 is shown as a positive value reflecting the actual patient work performed. The figure shows the inadequacy of using pressure time products of two breaths. FIG. 18 shows actual data taken from a sedated pig. The pig was heavily sedated to completely suppress natural respiratory drive. The pig was otherwise healthy and normal not presenting a complicated disease state. It was observed over the course of several hours that the diaphragm became weaker. At 1:3 selected breath ratio was selected and the pig stimulated at a level reflecting healthy normal work of breathing. In comparison with a control the measure work of breathing (not shown) was consistent between breaths the stimulation protocol reflected by stimulus 800 for selected breath 802. Repeated periodically on a 1:3 selection basis improved and persevered diaphragm function. To the investigators this suggests that selection ratios above 1:2 are beneficial and that an optimum may be found for clinical practice. In the experiment accelerometers were placed on the diaphragm and the waveform complex 804 and 806 reflect capture and effective stimulation at the parameters selected for stimulation.

FIGS. 19A, 19B, and 19C is a table showing the input parameters for the GUI.

Certain setting such as group 900 may be directly set by the user while group 904 will need to entered manually. Group 902 represents the expected waveform data to be presented to the user.

Risks Associated with Therapy

There are a number of risks associated with the therapy. The FIG. 20A and FIG. 20B present these risks in a tabular format with associated alarm conditions. These risks may result from user misuse or from a fault condition in the system. For instance, electrical stimulation may occur for too long a period if there is water in the patient circuit and it tricks the PEPNS system into thinking the patient is continuously inhaling. Water may offset one of the differential flow sensor pressure lines resulting in what looks like a continuous flow. Such an issue could also occur if the wye becomes disconnected and the ventilator continues to deliver flow until the ventilator detects that a disconnect has occurred. Water in the circuit may also cause auto trigger resulting in a high respiratory rate. Water in the circuit can causes a sloshing motion that results in air flow moving forwards like it does during inhalation and reversing as the water wave reverses simulating an exhalation. This motion may be misinterpreted by the ventilator as a patient effort resulting in the ventilator falsely triggering inspiration. The user may also forget to connect the flow sensor and wye sensor at the wye during suctioning of the patient resulting in the PEPNS system, failing to deliver electrical stimulation because the wye sensor is no longer connected to the wye. Also, if the patient's respiratory mechanics changes, there exists the potential that the patient will increase their level of work or reduce their level of work outside a level desired by the physician. Alarms already exists in pacing devices for lead impedance and device failures due to over current. Providing stimulation in conjunction with ventilation creates a requirement for additional safety measures to bring the user's attention to erroneous conditions. There exists a need to bring these alarm conditions to the user attention and to prevent erroneous electrical stimulation. The following alarms shown in FIG. 20A (A, A1 and A2 to be viewed as a continuity) and FIG. 20B have been implemented to prevent such conditions. The following headings are shown in the table:

Alarm Name: Name of alarm displayed to user.

Detection Criteria: criteria used to detect the alarm condition.

Description: Description of what the user is instructed to do when the alarm condition is detected.

Alarm Reaction: The PEPNS system reaction to the alarm. Upon annunciation of the alarm, the PEPNS system may enter a safe state where the drive to the electrical output is disabled or the device may continue operation. The reaction chosen is a function of the residual risk to the patient.

Enable/Disable Alarm: User has the ability to enable/ disable specific alarms as part of device if the alarm condition is duplicated on the ventilator. For instance, most ventilators will have an apnea alarm and this alarm will only need be invoked if the ventilator does not have such an alarm. Duplicating alarms will cause user frustration so giving the ability to disable these alarms will greatly improve usability of the device.

Name/Units: This section describes the units in which the alarm is set.

Range: This section describes the range of the alarm setting.

Giving the user the ability to detect changes in patient effort allows the user to detect loss of stimulation or changes in patient respiratory mechanics. The risks exist that the patient's respiratory mechanics may deteriorate after the initiation of therapy as a result of the disease progression, alerting the user to these conditions and not casing the patient to overexert the level of effort they are being requested to exert during stimulation will greatly improve device usability and decrease the risk of using the device on the patient. If the patient is repositioned during therapy stimulation may longer be effective. Alerting the user to this affect will ensure continuation of therapy and make the device more usable. The ICU is a complicated environment and deskilling the detecting of fault conditions is critical to usability. Detecting such fault conditions are only possible if the correct measurements and detections methods are made. It is also important to not make the detection too sensitive such that false positive alarms are detected.

Definitions

In the field of respiration there is not complete uniformity in the use of terms or nomenclature. This especially true with ventilation modes where manufacturers describe operation in terms of company specific nomenclature. To clarify the disclosure the following terms should be given the ascribed meaning in interpreting this document.

Work of Breathing—in this disclosure relates to the energy expended to inhale a breathing gas. It is usually expressed as work per unit volume, for example, joules/liter, or as a work rate (power), such as joules/min. In most instances the term relates to a single breath. In most literature it is measured over several breaths.

Work—It is usually expressed as work joules or it may also be expressed as the work per unit volume, for example, joules/liter.

Power—defines as the rate of work such as joules/min

Equation of Motion for Respiration is used to describe the pressures exerted by the compliance and resistive forces of the lung.

Selected breath. The stimulator controller intervenes by selecting a breath to stimulate this is done by selecting every other breath in simple ratio of 1:2 up to about a one of every twenty breaths (1:20)

Predecessor breath is the breath immediately prior to a selected breath.

Subsequent breath is the breath immediately after a selected breath.

Companion breath. From the perspective of a selected breath both predecessor breaths and subsequent breaths are defined as companion breaths. In essence all non selected breaths are companion breaths with the immediately following and preceding breaths given unique names.

Pressure control modality—is a mode of mechanical ventilation alone and a variable within other modes of mechanical ventilation. Pressure control is used to regulate pressures applied during mechanical ventilation. During Pressure Control Ventilation, the control parameter is pressure and flow is adjusted to reach the specified pressure.

Flow control modality—is used in Volume Control Ventilation. Various flow control modes may be used such as square wave or descending ramp. During Volume Control Ventilation, the control parameter is flow and pressure is a resultant parameter.

SIMV—Synchronized intermittent mechanical ventilation (SIMV) is a variation of IMV, in which the ventilator breaths are synchronized with patient inspiratory effort if the patient is making an effort to inspire. The breath mode is most often a mandatory breath mode paired with a spontaneous breath mode.

SIMV (Volume Control, PSV)—In this SIMV case the mandatory or assist mode of ventilation is a Volume Control breath with a spontaneous mode of Pressure Support Ventilation.

SIMV (Pressure Control, PSV)—In this SIMV case the mandatory or assist mode of ventilation is a Pressure Control breath with a spontaneous mode of Pressure Support Ventilation.

Bi-level Ventilation—Bilevel positive airway pressure (BPAP), commonly referred to by the trademarked names BiPAP and BiPAP, is a form of non-invasive mechanical pressure support ventilation that uses a time-cycled or flow-cycled change between two different applied levels of positive airway pressure.

PEEP—Positive end-expiratory pressure (PEEP) is the pressure in the lungs (alveolar pressure) above atmospheric pressure (the pressure outside of the body) that exists at the end of expiration.

Mandatory Breath—A breath for which either the timing or size is controlled by a ventilator; the machine initiates (i.e., triggers) or terminates (i.e., cycles) the breath.

Spontaneous Breath—During mechanical ventilation, a breath for which both the timing and the size are controlled by the patient (i.e., the breath is both initiated [triggered] and terminated [cycled] by the patient).

PRVC (Pressure Regulated Volume Control)—is a controlled mode of ventilation which combines pressure and volume controlled ventilation. A preset tidal volume is delivered at a set rate, similar to VC, but it is delivered with the lowest possible pressure.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the following numbered paragraphs, as well as in the claims below.

Paragraph 1. A lead system for use with a PEPNS system comprises the following elements: A first lead having a housing, the housing containing at least two or more pacing electrodes spaced apart in a linear arrangement; and an identifying resistor. Each of the pacing electrodes and identifying resistor being in separate electrical communication with a controller of the PEPNS system.

Paragraph 2. The system of paragraph 1 further comprising a second lead.

Paragraph 3. The system of paragraph 2 wherein the controller comprises an electrical pulse generator. Each electrode is in electrical communication with electrical pulse generator.

Paragraph 4. The system of paragraph 3 wherein the controller comprises a CPU and a GUI. The CPU is in electrical communication with each electrode, each identifying resistor, and the pulse generator. The CPU controls the characteristics of an electrical pulse sent to the first lead and the second lead. The GUI in electronic communication with the CPU.

Paragraph 5. A medical device for use with a mechanical ventilator where both the device and the ventilator are coupled to a patient; the medical device comprises: A multiple pole electrode set located on a lead. The lead is positioned subcutaneously and proximate at least one phrenic nerve in the neck of the patient. A stimulator/controller connected to the lead for selecting one electrode pair from the multiple pole electrode set, and defining a selected electrode pair and for delivering electrical stimulation to the selected electrode pair of the electrode set, according to a set of input electrical parameters that set a pulse repetition rate, a current amplitude, a pulse width, a pulse waveform, a stimulation pulse train waveform. The input electrical parameters sufficient to at least partially activate the patient's diaphragm. An instrumented wye coupled to the patient and coupled to the mechanical ventilator providing a wye flow measurement and a wye pressure measurement to the stimulator/controller. The stimulator/controller selecting one of several breaths, to define a single selected breath. The stimulator/controller initiating electrical stimulation in the single selected breath at the time that corresponds to a beginning of inspiration event triggered by a wye flow measurement. The stimulator/controller terminating electrical stimulation in the single selected breath at the time corresponding to an end of inspiration event triggered by the wye flow measurement. The beginning of the inspiration event of the selected breath and the end of inspiration event of the selected breath together setting a duration for the electrical stimulation within the inspiratory phase of a single selected breath cycle. A power/work measuring device within the stimulator/controller and coupled to the instrumented wye receiving a measured wye flow value, and a wye pressure value, defining a set of instrumented wye measurements. The power/work measurement device using the wye measurements along with a measure of lung compliance and a measure of lung resistance of the patient to predict a pressure curve in the wye over the duration. The power/work measurement device comparing the actual wye pressure curve to the predicted wye pressure curve and forming the difference between the predicted wye pressure and the actual measured wye pressure defining a Pmus value. The power/work measurement device using the Pmus value along with a measure of lung compliance and a measure of lung resistance of the patient to compute a work of breathing curve for the selected inspiratory phase of the single selected breath defining a work/power curve. The work/power curve representing the instantaneous work and associated time based power measurement representing the total power expended by the patient during the inspiratory duration of the selected breath without regard to the contribution to work performed by the mechanical ventilator.

Paragraph 6. A medical device for use with a mechanical ventilator, wherein both the device and the ventilator are coupled to a patient; the medical device comprises: A subcutaneous electrode pair positioned proximate at least one phrenic nerve in the neck of the patient. A stimulator/controller delivering electrical stimulation to the electrode pair at a pulse repetition rate, with a current and a waveform sufficient to at least partially activate the patient's diaphragm. An instrumented wye coupled to the patient and coupled to the mechanical ventilator, providing a wye flow measurement and a wye pressure measurement to the stimulator/controller. The stimulator/controller selecting one of several breaths defining a selected breath. The stimulator/controller beginning stimulation at the beginning of an inspiratory event in response to an inspiratory trigger event, the event corresponding to a preset specific flow at the instrumented wye. The stimulator/controller ending stimulation at the end of an concluded inspiratory event triggered by an end inspiratory trigger event, the event corresponding to a specific flow at the instrumented wye. The inspiratory event trigger and the end inspiratory event trigger and together defining a duration for the stimulation within the inspiratory phase of a single selected breath. A power/work measuring device coupled to the instrumented wye measuring the instantaneous work throughout the inspiratory phase of the single breath, by comparing a predicted pressure at the wye and a measured pressure at the wye, and indicating work only if the predicted pressure differs from the measured pressure at the instrumented wye.

Paragraph 7. The device of paragraph 6 wherein the inspiratory trigger is a patient initiated event.

Paragraph 8. The device of paragraph 6 wherein the end inspiratory trigger is a patient initiated event.

Paragraph 9. The device of paragraph 6 wherein the inspiratory trigger is a mechanical ventilator initiated event.

Paragraph 10. The device of paragraph 6 wherein the end inspiratory trigger is a mechanical ventilator initiated event.

Paragraph 11. The device of paragraph 6 further including an indicator presenting the level of stimulation delivered during the inspiration phase of the breath.

Paragraph 12. The device of paragraph 6 further including an indicator presenting the measured total power and total work for the level of stimulation delivered during the inspiration phase of the breath.

Paragraph 13. A medical device system for use with a mechanical ventilator, wherein both the system and the ventilator are coupled to a patient; the medical device system comprises: A mechanical ventilator operable in pressure control modes. A temporary electrode pair positioned subcutaneous and proximate at least one phrenic nerve in the neck of the patient. A stimulator/controller connected to electrode pair of the electrode set, according to a set of input electrical parameters that set a repetition rate, a current amplitude, a pulse width, a pulse waveform, a stimulation pulse train waveform, the input electrical parameters sufficient to at least partially activate the patient's diaphragm. The stimulator/controller including a power/work measurement device. An instrumented wye coupled to the patient and providing a wye flow measurement and a wye pressure measurement to the power/work measurement device within the stimulator/controller. The stimulator/controller selecting one of several breaths, defining a selected breath. The selected breath followed by a subsequent breath, defining a subsequent breath. The stimulator/controller initiating electrical stimulation at the beginning of the selected breath that corresponds to an inspiratory event triggered by a wye flow measurement. The stimulator/controller terminating electrical stimulation at the end of an inspiratory event triggered by the wye flow measurement. The beginning inspiratory event of the selected breath and the ending inspiratory event of the selected breath together setting a stimulation duration for the inspiratory phase of the single selected breath. A power/work measuring device within the stimulator/controller and coupled to the instrumented wye receiving wye pressure and flow measurement and displaying a positive value for work during a stimulated breath. The mechanical ventilator initiating a pressure control subsequent breath. The mechanical ventilator terminating the subsequent pressure control breath defining a pressure control subsequent breath duration having a characteristic pressure control profile. The power/work measurement device determining a zero value for work during the subsequent pressure control breath.

Paragraph 14. A medical device system for use with a mechanical ventilator both coupled to a patient, the medical device system comprises: A mechanical ventilator operable in volume control modes. A temporary electrode pair positioned subcutaneously and proximate to at least one phrenic nerve in the neck of the patient. A stimulator/controller connected to electrode pair of the electrode set, according to a set of input electrical parameters that set a repetition rate, a current amplitude, a pulse width, a pulse waveform, a stimulation pulse train waveform. The input electrical parameters sufficient to at least partially activate the patient's diaphragm. The stimulator/controller including a power/work measurement device. An instrumented wye coupled to the patient providing a wye flow measurement and a wye pressure measurement to the power/work measurement device within the stimulator/controller. The stimulator/controller selecting one of several breaths, defining a selected breath. The selected breath followed by subsequent next breath, defining a sequential breath. The stimulator/controller initiating electrical stimulation at the beginning of the selected breath that corresponds to an inspiratory event triggered by a wye flow measurement. The stimulator/controller terminating electrical stimulation at the end of an inspiratory event triggered by the wye flow measurement. The beginning inspiratory event of the selected breath and the ending inspiratory event of the selected breath together setting a duration for the electrical stimulation within the inspiratory phase of a single selected breath cycle. A power/work measuring device within the stimulator/controller and coupled to the instrumented wye receiving wye pressure measurement and displaying a positive value for work during a stimulated breath. The mechanical ventilator initiating a volume control breath. The power/work measurement device using the wye pressure measurement and displaying a zero value for work during the volume control breath.

Paragraph 15. A method of stimulating a diaphragm to provoke motion of the diaphragm during inspiration comprises the following steps:
  a. stimulating the phrenic nerve at a set level during a selected breath of a patient;
  b. obtaining a measurement of the diaphragm work exerted by the patient for the inspiratory breath cycle of a selected breath of a patient;
  c. modifying the stimulation signal if the actual value of diaphragm work is outside the selected range of the desired value of diaphragm work; and repeating steps a-c.

Paragraph 16. A medical device for use with a mechanical ventilator wherein both are coupled to a patient. The medical device comprises: A multiple pole electrode set located on a lead, wherein the lead is positioned subcutaneously and proximate to at least one phrenic nerve in the neck of the patient. A stimulator/controller connected to the lead for selecting one electrode pair from the multiple pole electrode set defining a selected electrode pair and for delivering electrical stimulation to the selected electrode pair of the electrode set, according to a set of input electrical parameters that set a pulse repetition rate, a current amplitude, a pulse width, a pulse waveform, a stimulation pulse train waveform. The input electrical parameters sufficient to at least partially activate the patient's diaphragm. An instrumented wye coupled to the patient and coupled to the mechanical ventilator providing a wye flow measurement and a wye pressure measurement to the stimulator/controller. The stimulator/controller selecting one of several breaths, defining a single selected breath. The stimulator/controller initiating electrical stimulation at the beginning of the selected breath that corresponds to an inspiratory event triggered by a wye flow measurement. The stimulator/controller terminating electrical stimulation at the end of an inspiratory event triggered by the wye flow measurement. The beginning inspiratory event of the selected breath and the ending inspiratory event of the selected breath together setting a duration for the electrical stimulation within the inspiratory phase of a single selected breath cycle. A power/work measuring device within the stimulator/controller and coupled to the instrumented wye receiving a measured wye flow value, and a wye pressure value, defining a set of instrumented wye measurements. The power/work measurement device using the wye measurements along with a measure of lung compliance and a measure of lung resistance of the patient to predict a pressure curve for the selected inspiratory phase of the selected breath defining a predicted wye pressure curve. The power/work measurement device comparing the actual wye pressure value to the predicted wye pressure curve and forming the difference between the predicted wye pressure and the actual measured wye pressure defining a Pmus value. The power/work measurement device using the Pmus value along with a measure of lung compliance and a measure of lung resistance of the patient to compute a work of breathing curve for the selected inspiratory phase of the single selected breath defining a work/power curve. The work/power curve representing the instantaneous work and associated time based power measurement representing the total power expended by the patient during the inspiratory phase of the selected breath without regard to the contribution to work performed by the mechanical ventilator.

Paragraph 17. A medical device for use with a mechanical ventilator both coupled to a patient. The medical device comprises: A subcutaneous electrode pair positioned proximate at least one phrenic nerve in the neck of the patient. A stimulator/controller delivering electrical stimulation to the selected electrode pair at a pulse repetition rate, with a current and a waveform sufficient to at least partially activate the patient's diaphragm. An instrumented wye coupled to the patient providing a wye flow measurement and a wye pressure measurement to the stimulator/controller. The stimulator/controller selecting one of several breaths defining a selected breath. The stimulator/controller beginning stimulation at the beginning of a patient initiated inspiratory event triggered by flow at the wye. The stimulator/controller ending stimulation at the end of a patient concluded inspiratory event triggered by flow at the wye. The patient initiated inspiratory event and the patient concluded inspiratory event thereby setting a duration for the stimulation within the inspiratory phase of a single selected patient initiated breath cycle. A power/work measuring device coupled to the instrumented wye measuring the instantaneous work throughout the inspiratory phase of the single breath, by comparing a predicted pressure at the wye and a measured pressure at the wye, and indicating work only if the predicted pressure differs from the measured pressure in the wye. An indicator presenting the level of stimulation delivered during the inspiration phase of the breath. An indicator presenting the measured total power and total work for the level of stimulation delivered during the inspiration phase of the breath.

Paragraph 18. A medical device for use with a mechanical ventilator both coupled to a patient. The medical device comprises: A subcutaneous electrode pair positioned proximate at least one phrenic nerve in the neck of the patient. A stimulator/controller delivering electrical stimulation to the selected electrode pair at a pulse repetition rate, a current and a waveform sufficient to at least partially activate the patient's diaphragm. An instrumented wye coupled to the patient providing a wye flow measurement and a wye pressure measurement to the stimulator/controller. The stimulator/controller selecting stimulator/controller g one of several breaths defining a selected breath. The stimulator/controller beginning stimulation at the beginning of the a patient initiated inspiratory event triggered by flow at the wye. The stimulator/controller ending stimulation at the end of a mechanical ventilator concluded inspiratory event triggered by flow at the wye. The patient initiated inspiratory event and the mechanical ventilator concluded inspiratory event thereby setting a duration for the stimulation within the inspiratory phase of a single selected patient initiated breath cycle. A power/work measuring device coupled to the instrumented wye measuring the instantaneous work throughout the inspiratory phase of the single breath, by comparing a predicted pressure at the wye and a measured pressure at the wye, and indicating work only if the predicted pressure differs from the measured pressure in the wye. An indicator presenting the level of stimulation delivered during the inspiration phase of the breath. An indicator presenting the measured total power and total work for the level of stimulation delivered during the inspiration phase of the breath.

Paragraph 19. A medical device for use with a mechanical ventilator both coupled to a patient. The medical device comprises: A subcutaneous electrode pair positioned proximate at least one phrenic nerve in the neck of the patient. A stimulator/controller delivering electrical stimulation to the selected electrode pair at a repetition rate, with a voltage, a current and a waveform sufficient to at least partially activate the patient's diaphragm. An instrumented wye coupled to the patient providing a wye flow measurement and a wye pressure measurement to the stimulator/controller. The stimulator/controller selecting one of several breaths defining a selected breath. The S/C beginning stimulation at the beginning of the mechanical ventilator initiated inspiratory event triggered by flow at the wye. The stimulator/controller ending stimulation at the end of a mechanical ventilator concluded inspiratory event triggered by flow at the wye. The patient initiated inspiratory event and the patient concluded inspiratory event thereby setting a duration for the stimulation within the inspiratory phase of a single selected patient initiated breath cycle. A power/work measuring device coupled to the instrumented wye measuring the instantaneous work throughout the inspiratory phase of the single breath, by comparing a predicted pressure at the wye and a measured pressure at the wye, and indicating work only if the measured pressure exceeds the predicted pressure in the wye. An indicator presenting the level of stimulation delivered during the inspiration phase of the breath. An indicator presenting the measured total power and total work for the level of stimulation delivered during the inspiration phase of the breath.

Paragraph 20. A medical device for use with a mechanical ventilator both coupled to a patient. The medical device comprises: A subcutaneous electrode pair positioned proximate at least one phrenic nerve in the neck of the patient. A stimulator/controller delivering electrical stimulation to the selected electrode pair at a pulse repetition rate, a current and a waveform sufficient to at least partially activate the patient's diaphragm. An instrumented wye coupled to the patient providing a wye flow measurement and a wye pressure measurement to the stimulator/controller. The stimulator/controller selecting one of several breaths defining a selected breath. The stimulator/controller beginning stimulation at the beginning of the mechanical ventilator initiated inspiratory event triggered by flow at the wye. The stimulator/controller ending stimulation at the end of a patient concluded inspiratory event triggered by flow at the wye. The ventilator initiated inspiratory event and the patient concluded inspiratory event thereby setting a duration for the stimulation within the inspiratory phase of a single selected patient initiated breath cycle. A power/work measuring device coupled to the instrumented wye measuring the instantaneous work throughout the inspiratory phase of the single breath, by comparing a predicted pressure at the wye and a measured pressure at the wye, and indicating work only if the predicted pressure differs from the measured pressure in the wye. An indicator presenting the level of stimulation delivered during the inspiration phase of the breath. An indicator presenting the measured total power and total work for the level of stimulation delivered during the inspiration phase of the breath.

Paragraph 21. The medical device of paragraph 9 which further comprises: A display presenting the level of stimulation delivered during the inspiration phase of the breath. A display presenting the measured total power and total work for the level of stimulation delivered during the inspiration phase of the breath.

Paragraph 22. A medical device system for use with a mechanical ventilator both coupled to a patient. The medical device system comprises: A mechanical ventilator operable in both pressure control and volume control modes. A temporary electrode pair positioned subcutaneous and proximate at least one phrenic nerve in the neck of the patient. A stimulator/controller connected to electrode pair of the electrode set, according to a set of input electrical parameters that set a repetition rate, a current amplitude, a pulse width, a pulse waveform, a stimulation pulse train waveform, the input electrical parameters sufficient to at least partially activate the patient's diaphragm; the stimulator/controller including a power/work measurement device. An instrumented wye coupled to the patient providing a wye flow measurement and a wye pressure measurement to the power/work measurement device within the stimulator/controller. The stimulator/controller selecting one of several breaths, defining a selected breath. The selected breath followed by subsequent next breath, defining a sequential breath. The stimulator/controller initiating electrical stimulation at the beginning of the selected breath that corresponds to an inspiratory event triggered by a wye flow measurement. The stimulator/controller terminating electrical stimulation at the end of an inspiratory event triggered by the wye flow measurement. The beginning inspiratory event of the selected breath and the ending inspiratory event of the selected breath together setting a duration for the electrical stimulation within the inspiratory phase of a single selected breath cycle. A power/work measuring device within the stimulator/controller and coupled to the instrumented wye receiving wye pressure and flow measurement and displaying a positive value for work during a stimulated breath. The mechanical ventilator initiating a pressure control breath. The mechanical ventilator terminating a pressure control breath at the wye. The beginning and ending forming a duration having a characteristic pressure profile. The power/work measurement device using the wye pressure measurement and displaying a zero value for work during an un-stimulated pressure control breath.

Paragraph 23. A medical device system for use with a mechanical ventilator both coupled to a patient. The medical device system comprises: A mechanical ventilator operable in both pressure control and volume control modes. A temporary electrode pair positioned subcutaneously and proximate to at least one phrenic nerve in the neck of the patient. A stimulator/controller connected to electrode pair of the electrode set, according to a set of input electrical parameters that set a repetition rate, a current amplitude, a pulse width, a pulse waveform, a stimulation pulse train waveform, the input electrical parameters sufficient to at least partially activate the patient's diaphragm; the stimulator/controller including a power/work measurement device. An instrumented wye coupled to the patient providing a wye flow measurement and a wye pressure measurement to the power/work measurement device within the stimulator/controller. The stimulator/controller selecting one of several breaths, defining a selected breath. The selected breath followed by subsequent next breath, defining a sequential breath. The stimulator/controller initiating electrical stimulation at the beginning of the selected breath that corresponds to an inspiratory event triggered by a wye flow measurement. The stimulator/controller terminating electrical stimulation at the end of an inspiratory event triggered by the wye flow measurement. The beginning inspiratory event of the selected breath and the ending inspiratory event of the selected breath together setting a duration for the electrical stimulation within the inspiratory phase of a single selected breath cycle. A power/work measuring device within the stimulator/controller and coupled to the instrumented wye receiving wye pressure measurement and displaying a positive value for work during a stimulated breath. The mechanical ventilator initiating a volume control breath. The power/work measurement device using the wye pressure measurement and displaying a zero value for work during an un-stimulated volume control breath.

Paragraph 24. A method of stimulating a diaphragm to provoke motion of the diaphragm during inspiration comprises the following steps:
 a. obtaining a measurement of the work exerted for the inspiratory breath cycle of a selected breath of a patient;
 b. setting a desired value for the level of work during contraction of the diaphragm, transmitting a stimulation signal to an electrode positioned within subcutaneous tissue of the patient such that the electrode recruits a phrenic nerve of the patient and contracts the diaphragm;
 c. after transmitting the stimulation signal, determining the actual work generated by the diaphragm;
 d. as a function of wye flow, pressure and patient resistance and compliance and maintaining the stimulation signal valve for later selected breaths if the actual value of the level of the diaphragm work is within a selected range of the desired value;
 or modifying the stimulation signal if the actual value of diaphragm work is outside the selected range of the desired value of diaphragm work; and repeating steps a-d.

What is claimed is:

1. A medical device for use with a mechanical ventilator and breathing circuit coupled to a patient, said medical device comprising:
 a subcutaneous electrode pair positioned proximate at least one phrenic nerve in the neck of said patient;
 a stimulator/controller connected to said electrode pair via a lead cable, said stimulator/controller delivering electrical stimulation to said electrode pair at a pulse repetition rate, with a current and a waveform sufficient to at least partially activate the patient's diaphragm;
 an instrumented wye coupled to said patient and coupled to said mechanical ventilator via tubing of the breathing circuit, providing a wye flow measurement and a wye pressure measurement to said stimulator/controller;
 said stimulator/controller selecting one of several breaths defining a single selected breath;
 said stimulator/controller beginning stimulation at the beginning of an inspiratory event in response to an inspiratory trigger event, said event corresponding to a preset specific flow at said instrumented wye;
 said stimulator/controller ending stimulation at the end of an inspiratory event triggered by an end inspiratory trigger event, said event corresponding to a specific flow at said instrumented wye;
 said inspiratory event trigger and said end inspiratory event trigger together defining a duration for the stimulation within the inspiratory phase of said single selected breath;
 a power/work measuring device coupled to said instrumented wye measuring the instantaneous work throughout the inspiratory phase of said single selected breath, by comparing a predicted pressure at the wye and a measured pressure at the wye, and indicating work only if the predicted pressure differs from the measured pressure at said instrumented wye.

2. The device of claim 1 wherein said inspiratory trigger event is a patient initiated event.

3. The device of claim 1 wherein said end inspiratory trigger event is a patient initiated event.

4. The device of claim 1 wherein said inspiratory trigger event is a mechanical ventilator initiated event.

5. The device of claim 1 wherein said end inspiratory trigger event is a mechanical ventilator initiated event.

6. The device of claim 1 further including:
 an indicator presenting the level of stimulation delivered during said duration of the single selected breath.

7. The device of claim 1 further including:
 an indicator presenting the measured total power and total work for the level of stimulation delivered during the said duration of said single selected breath.

* * * * *